US009337514B2

(12) United States Patent
Johnson et al.

(10) Patent No.: US 9,337,514 B2
(45) Date of Patent: May 10, 2016

(54) ELECTROPOLYMERIZATION OF A COATING ONTO AN ELECTRODE MATERIAL

(71) Applicants: COLORADO STATE UNIVERSITY RESEARCH FOUNDATION, Fort Collins, CO (US); PRIETO BATTERY, INC., Fort Collins, CO (US)

(72) Inventors: Derek C. Johnson, Johnstown, CO (US); Amy L. Prieto, Fort Collins, CO (US); Matthew Rawls, Aurora, CO (US); Daniel J. Bates, Fort Collins, CO (US); C. Michael Elliott, Fort Collins, CO (US)

(73) Assignees: Colorado State University Research Foundation, Fort Collins, CO (US); Prieto Battery, Inc., Fort Collins, CO (US)

( * ) Notice: Subject to any disclaimer, the term of this patent is extended or adjusted under 35 U.S.C. 154(b) by 79 days.

(21) Appl. No.: 14/059,148

(22) Filed: Oct. 21, 2013

(65) Prior Publication Data

US 2014/0173889 A1   Jun. 26, 2014

Related U.S. Application Data

(60) Provisional application No. 61/715,943, filed on Oct. 19, 2012.

(51) Int. Cl.
| | |
|---|---|
| *H01M 10/0585* | (2010.01) |
| *H01M 10/0525* | (2010.01) |
| *H01M 2/14* | (2006.01) |
| *H01M 2/16* | (2006.01) |
| *C25D 11/00* | (2006.01) |
| *G01N 27/26* | (2006.01) |

(52) U.S. Cl.
CPC ........... *H01M 10/0585* (2013.01); *G01N 27/26* (2013.01); *H01M 2/145* (2013.01); *H01M 2/1653* (2013.01); *H01M 10/0525* (2013.01); *Y10T 29/49115* (2015.01)

(58) Field of Classification Search
None
See application file for complete search history.

(56) References Cited

U.S. PATENT DOCUMENTS

| | | |
|---|---|---|
| 6,589,299 B2 | 7/2003 | Missling et al. |
| 6,986,967 B2 | 1/2006 | Barton et al. |
| 7,361,431 B2 | 4/2008 | Kim et al. |
| 7,858,379 B2 | 12/2010 | Vaidya |
| 8,119,542 B2 | 2/2012 | Mevellec et al. |
| 8,231,710 B2 | 7/2012 | Kase et al. |
| 2007/0212603 A1 | 9/2007 | Nathan et al. |
| 2007/0289872 A1 * | 12/2007 | Deniau et al. ................. 205/157 |
| 2008/0124832 A1 | 5/2008 | Deniau et al. |
| 2008/0241705 A1 | 10/2008 | Wakita et al. |
| 2012/0042953 A1 | 2/2012 | Nishimura et al. |
| 2012/0073971 A1 | 3/2012 | Prieto et al. |

FOREIGN PATENT DOCUMENTS

| | | |
|---|---|---|
| EP | 0542836 B1 | 11/1995 |
| WO | 9429873 A2 | 12/1994 |
| WO | WO 2009105773 A2 * | 8/2009 |

OTHER PUBLICATIONS

International Search Report, International Searching Authority, pp. 1-28, Feb. 21, 2014.

* cited by examiner

*Primary Examiner* — Gregg Cantelmo
(74) *Attorney, Agent, or Firm* — Samuel M. Freund; Cochran Freund & Young, LLC

(57) ABSTRACT

Methods for reductively polymerizing vinylic based monomers from a solution thereof onto the surface of an electrode material, resulting in thin, electrically insulating solid-polymer electrolyte coatings strongly bound to the surface of the electrode material, are described. The strong bond permits a second electrode to be coated directly onto the solid-polymer electrolyte, thereby incorporating the required components for a Li-ion battery cell. At least one initiator species, which is readily reduced by accepting an electron from the electrode material, is included in electropolymerization deposition solution for permitting the polymerization of vinylic species that would otherwise not electrochemically polymerize without damage to either the electrode material or to the solvents employed.

62 Claims, 13 Drawing Sheets

ELECTROPOLYMERIZATION OF A COATING ONTO AN ELECTRODE MATERIAL

CROSS-REFERENCE TO RELATED APPLICATIONS

The present application claims the benefit of U.S. Provisional Patent Application No. 61/715,943 for "Methods For Electropolymerizing A Solid Polymer Electrolyte And Use Within Lithium-Ion Batteries," by Daniel J. Bates et al., which was filed on Oct. 19, 2012, the contents of which application is hereby specifically incorporated by reference herein for all that it discloses and teaches.

FIELD OF THE INVENTION

Embodiments of the present invention relates generally to electrodeposition of solid-state coatings onto electrically conducting materials and, more specifically, to the electropolymerization of solid-state electrolytes onto electrodes effective for use in solid-state Li-ion battery cells.

BACKGROUND OF THE INVENTION

Achieving high power densities in Li-ion batteries requires increasing the charge and discharge rates. The two principal transport properties limiting these rates are the slow solid-state diffusion of Li-ions into the negative and positive electrodes and the slow diffusion between the electrodes. Slow solid-state diffusion processes within electrodes, may be mitigated by decreasing the features of both electrodes to the nanoscale, and the electrode morphologies of choice having high surface-to-volume ratios such as nanoparticles and nanowires. Although reducing the battery electrode features to the nanoscale has resulted in incremental improvements, decreasing the characteristic Li-ion diffusion length between the electrodes while maintaining the micro-nanoscale electrode morphology has not, and thus three-dimensional (3D) battery morphologies have been proposed. To fabricate a solid-state 3D Li-ion battery cell, an appropriate electrode material is deposited on a 3D current collector, the architecture of the current collector, which can be tailored, establishing the overall cell morphology and is the building block of the other cell components. A tailorable architecture provides the ability to tune the cell properties for specific applications based on performance metrics such as cost, power density, energy density, safety, and cell life.

In 3D architectures, interdigitated electrodes are separated by a thin conformal solid-state electrolyte onto which electrolyte one of the electrodes is directly applied, and require fabrication control such that a uniform, thin, and pinhole free electrolyte coating is generated. Electrodeposition provides a suitable coating process for such solid state electrolyte materials, since it is well understood, permits control of thickness, provides uniform coatings on complex and 3D surfaces, and has been demonstrated to be cost effective.

SUMMARY OF THE INVENTION

Embodiments of the present invention overcome the disadvantages and limitations of prior art by providing a method for electrodeposition of uniform, thin, pinhole-free, Lithium-ion permeable solid-state electrolytes on conducting materials.

Another object of embodiments of the present invention is to provide a method for electrodeposition of solid-state electrolytes on 3D interpenetrating electrodes.

Yet another object of embodiments of the present invention is to provide a method for electrodeposition of solid-state electrolytes on electrodes effective for use in Lithium-ion batteries.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects, and in accordance with the purposes of embodiments of the present invention, as embodied and broadly described herein, the method for electrochemically depositing an ionically conducting, electrically insulating coating onto the surface of an electrode material, hereof, includes: submersing the electrode material into a solution comprising at least one initiator species dissolved in a solvent, wherein the initiator species is capable of being reduced forming a radical species when an electron is injected from the electrode material into the at least one initiator species, and wherein the at least one reduced initiator species is chemisorbed onto the electrode material surface; and at least one monomeric species having at least one vinyl group, or vinyl group derivative, thereon; submersing a second electrode into the solution; and applying an electric potential between the electrode material and the second electrode effective for reducing the at least one initiator species; whereby polymerization of the at least one monomeric species is induced by the reduction of the at least one initiator species forming a coating which is bonded to the surface of the electrode material.

In another aspect of embodiments of the present invention, and in accordance with its objects and purposes, the method for producing a lithium-ion battery, hereof, includes: submersing an electrode comprising electrodeposited $Cu_2Sb$ active material into a solution comprising at least one initiator species dissolved in a solvent comprising water, wherein the at least one initiator species is capable of being reduced forming a radical species when an electron is injected from the $Cu_2Sb$ active material into the at least one initiator species, and wherein the reduced initiator species is chemisorbed onto a surface of the $Cu_2Sb$ active material; and at least one monomeric species having at least one vinyl group, or vinyl group derivative thereon; submersing a second electrode into the solution; applying an electric potential between the electrode material and the second electrode effective for reducing the at least one initiator species; whereby polymerization of the at least one monomeric species is induced by the reduction of the initiator species forming a $Li^+$-conducting and electrically insulating coating which is bonded to the surface of the active material; preparing an solution-based slurry comprising at least one cathode material; contacting the coating with the slurry; drying the coating material onto which the at least one cathode material has been deposited; and placing a current collector in electrical communication with the at least one cathode material.

Benefits and advantages of the present invention include, but are not limited to methods for electrochemically depositing an ionically conducting, electrically insulating coating onto the surface of an electrode material, wherein at least one initiator species is a component of the electropolymerization deposition bath that permits the polymerization of a at least one vinylic species (monomers) that would otherwise not electrochemically polymerize without damage to either the electrode material or the solvents. Further, the at least one initiator species affects polymerization rates and degree of polydispersity, as well as having an effect on other properties of the final solid polymer electrolyte coating due to the at least one initiator being dispersed in the polymer film during the electropolymerization processes and its incorporation into the resulting solid polymer electrolyte. Therefore, the film characteristics of the solid polymer electrolyte are a function of the monomers and the initiators. The monomer types and concentrations in the electropolymerization bath may also be varied to induce desired film properties.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
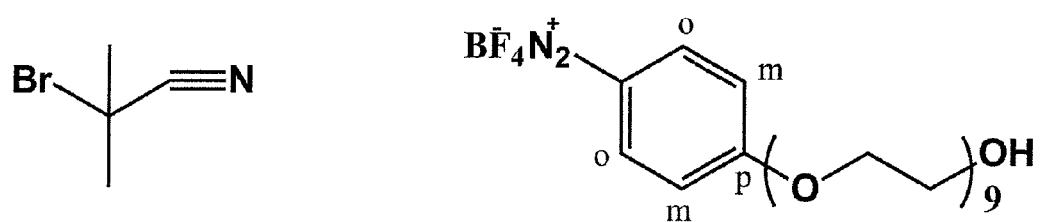
FIG. 1 shows the structures of bromoisobutyronitrile and p-poly(ethylene glycol) benzene diazonium tetrafluoroborate as well as the assignments of the ortho-, meta-, and para-locations on the benzene ring for the diazonium based species.

Embodiments of the present invention include methods for reductively polymerizing vinylic based monomers onto the surface of an electrode from an aqueous solution, resulting in thin, solid polymer electrolyte coatings strongly bound to the surface of the electrode. The strong bond allows a second electrode to be coated directly onto the solid polymer electrolyte, thereby incorporating the required components for a Li-ion battery cell. In particular, solid-state electrolytes may be electrodeposited onto 3D interpenetrating electrodes.

The function of a solid-state electrolyte in Lithium-ion batteries is to electrically isolate the negative and positive electrodes while allowing Li-ions to be readily transported through the electrolyte to the surface of the electrodes. An increase in power density of several orders of magnitude is expected for the use of 3D structured electrodes having micron- to nanometer scale dimensions. It should be mentioned that the present disclosed methods may also be used in the fabrication of two-dimensional (2D) battery structures, as well as structures having characteristic dimensions larger than the nanoscale, such as copper foam or other metal foams.

Electropolymerization of ionically conducting dielectric polymers extends basic electrodeposition methods to battery electrolytes, by providing defect-free, uniform films. Such depositions are self-limiting because polymerization occurs on bare electrode regions and ceases once a thickness is reached which can block electron flow, resulting in a uniform modification of the conducting surface with a polymer coating that exhibits the properties of the monomers in the deposition solution.

Many electropolymerization procedures are based on oxidative processes which occur at potentials sufficiently positive to induce damage to materials, such as tin, and many intermetallic compounds that are proposed higher capacity replacements for carbon based anodes in Li-ion batteries. Electroreductive polymerizations take place at voltages more negative than the material oxidation potential. For example, direct electroreductive polymerization of vinylic functionalized monomers occurs at potentials that do not induce oxidative damage to materials are expected to be useful as replacement anode materials. However, vinyl functional groups generally undergo reduction (and radical polymerization) at potentials more negative than the electrochemical solvent window of water, thereby requiring rigorously controlled anhydrous conditions, often in toxic organic solvents.

Although the term "electrolyte" is utilized extensively herein, those having skill in appropriate art areas would understand that the methods for electropolymerization of films hereof find use for generating anti-corrosion coatings and other purposes, in addition to use as electrolytes for the conduction of positive ions, such as $Li^+$ ions. The term "electrolyte" therefore not only has its customary meaning as applied to electrochemical devices, but is also more generally applied to the film that results upon use of the methods described herein. The context of each use of this term should make its meaning clear.

Aspects of the present electropolymerization methods including deposition species, deposition procedures, and deposition cell setup, will now be described, along with applications to an all solid-state polymer-based separator (SPE) for use in lithium-ion batteries. As further described below, at least one initiator is a component of the electropolymerization deposition bath that permits the polymerization of vinylic species (monomers) that would otherwise not electrochemically polymerize without damage to either the electrode material or the solvents. Additionally, the at least one initiator species affects polymerization rates and degree of polydispersity, as well as other properties of the final solid polymer electrolyte coating, due to the at least one initiator being dispersed in the polymer film during the electropolymerization processes and its incorporation into the resulting solid polymer electrolyte. Therefore, the film characteristics of the solid polymer electrolyte are a function of the monomers and the initiators. The monomer types and concentrations in the electropolymerization bath are also varied to induce desired film properties.

The functionality of the solid-polymer electrolyte films hereof is realized by incorporating a crosslinking agent, which improves chemical stability of the electropolymerized films, incorporating lithium cation-containing monomers for improving the transference number thereof, and incorporating lithium salt solvating functional groups, more specifically poly-ethylene glycol branches, for improving the ionic conductivity of the film at room temperature. As will be described hereinbelow, control of the deposition provides thinner solid polymer electrolyte films which adhere more strongly to the surface of the $Cu_2Sb$ working electrode, resulting in a higher cell fabrication success rate since application of a second electrode is less likely to damage a solid polymer electrolyte coating that is strongly bonded to the surface of the first electrode.

A. Films Containing only an Initiator:

An embodiment of the present invention uses at least one initiator species that can be electrochemically reduced when an electron is injected from a conducting working electrode, thereby resulting in a grafted or chemisorbed species, which may promote further electropolymerization. Initiators are chosen such that the bond strength between the initiator species and the surface of the working electrode can resist processes that would otherwise remove a physisorbed species from the surface of the working electrode. These processes include, but are not limited to, severe rinsing and sonication in a variety of solvents. Covalent bonds, as well as other physical interactions that are stronger than physisorption (that is, pi-pi, ionic, and dipole-dipole interactions) are formed by the chosen initiators. Examples of initiator species that can be utilized include reductively activated radical species such as aromatic diazonium salts, aromatic iodonium salts, potassium persulfate/$H_2SO_4$, and halogenated isobutyronitrile (such as bromoisobutyronitrile). Examples of cations for diazonium salts include 4-methoxybenzenediazonium and 4-nitrobenzenediazonium, while anions include tetrafluoroborate. The above mentioned species do not form an exhaustive list. The anion and cation of the diazonium based initiator species can be tailored in a way that the potential for which the electron is injected from the working electrode can be tuned. In addition to the reduction potential, the solubility of the initiator species in various solvents can also be tailored through selection of the cation and anion. Upon reduction of the initiator at the electrode surface, a covalent bond is formed with the working electrode surface, while a radical that will induce polymerization at the electrode surface of other monomer species contained in the deposition solution, such as vinylic monomers, is simultaneously formed. As mentioned hereinabove, the reduction potentials of vinylic species are generally significantly more negative than the reduction potential of the initiator species. Thus, embodiments of the present invention enable electropolymerization of monomers whose reduction potential is outside the electrochemical window required by the solvent and the working electrode.

In the description that follows, the working electrode is $Cu_2Sb$ and the solvent can include aqueous and organic solvents: It should be noted however, that embodiments of the present invention include other working electrodes that are electrically conducting, including those that are active anode materials for Li-ion batteries. Additionally, while these embodiments can be extended to non-aqueous solvents, the description that follows will focus on the electropolymerization of coatings from aqueous deposition solutions. In general, electropolymerization of the initiator species onto the surface of the working electrode, when utilizing reductive techniques, should be performed at a potential that is more positive than the electrochemical reduction potential of the solution and more negative than the electrochemical oxidation potential of the working electrode. Thus, when discussing electropolymerizing an initiator species onto the surface of $Cu_2Sb$ from an aqueous solution, the species should be reduced at a potential that is more positive than the electrochemical reduction of water and more negative than the oxidation potential of $Cu_2Sb$. The electrochemical reduction potential of water on the surface of $Cu_2Sb$ is pH dependent. As a guide for neutral and slightly acidic aqueous solutions, the potential for the initiator species reduction should be more positive than −1 V vs. Ag/AgCl. The oxidation of $Cu_2Sb$ occurs at potentials greater than or equal to approximately −0.3 V vs. Ag/AgCl. Also as a guide, it is advantageous to use a reduction potential more negative than −0.3 V vs. Ag/AgCl. Two examples of diazonium species that meet these criteria in addition to being soluble in water are 4-methoxybenzenediazonium tetrafluoroborate and 4-nitrobenzenediazonium tetrafluoroborate. These two examples do not represent all of the possible initiator species. In fact, any initiator species will be acceptable as long as the species meets the above described criteria. In addition to tailoring the reduction potential and solubility of the initiator species, the initiator can also be functionalized to induce Li-ion conductivity. Inducing Li-ion conductivity is described in detail hereinbelow.

A range of initiator concentrations can result in a chemisorbed film. However, to achieve full coverage especially on high surface area electrodes, a range of approximately 1 mM to 50 mM will ensure that there are sufficient initiator molecules in solution to result in a conformal, defect free coating. As a guide, lower concentrations will require longer deposition times, but result in a more uniform coating. Conversely, higher concentrations require shorter deposition times but result in less uniform coatings that could require post-annealing. Electropolymerization of an initiator species onto a working electrode can be a self-limiting process, with resulting film thicknesses being nanoscale because electropolymerized initiator species are generally electrical insulators. As a result, the growth process ceases once electrons required for the electropolymerization can no longer pass through the insulating film. The final thickness of the deposited film will vary and will be a function of the initiator species as well as the solvent. To electrochemically graft an initiator species to the surface of a working electrode, potentiostatic techniques may be advantageous in order to ensure that the initiator is appropriately reduced, that the potential remains in the electrochemical window of the solvent, and that the working electrode is not damaged through electrochemical oxidation or reduction.

When using potentiostatic electrochemical deposition, a voltage corresponding to the reduction of the initiator species, which can be tailored and is a function of initiator species, is applied until current can no longer be passed through the system. A zero current indicates that the surface of the working electrode has been completely covered with electrically insulating, covalently bonded initiator species. During electrochemical reduction of an initiator species, gas evolution is occasionally observed. As a result, multiple potentiostatic electropolymerization cycles may be performed while ensuring that any gas formed and adhered to the surface is removed between cycles. Additionally, because the electrochemically deposited film can be permeated by the deposition solvent, a current of zero is difficult to obtain even though the film is electrically insulating. Thus, a current that asymptotically reaches a non-zero steady state value may be used as the criteria for which the applied potential is extinguished, and deposition is complete. It should be noted that the number of cycles and the minimal current value will be a function of the initiator species, and optimum values for each should be determined for each species. Specific application of this embodiment utilizing 4-methoxybenzenediazonium tetrafluoroborate dissolved in water with $Cu_2Sb$ as the working electrode is described in EXAMPLE 1, hereinbelow.

It should be noted that while initiator only films may be suitable for anti-corrosion and other purposes, the coatings produced in this manner were not useful for solid-state lithium-ion cells, perhaps due to the thin coatings (approximately 10 nm) generated, which were found not to be able to withstand the application of the second electrode directly to the coating surface to complete the cell without damage, resulting in an internal electrical short.

B. Films Generated Using Initiator and Monomer(s):

Another embodiment of the invention utilizes the covalently bonded species generated in Section A, hereinabove, for inducing polymerization of monomer species also dissolved in the deposition solution containing at least one vinyl group or a derivative thereof, such as acrylate or methacrylate, on the surface of the working electrode. The resulting coating comprising the initiator species and any additional polymer species in the deposition solution is also covalently bonded to the surface of the working electrode. The solvent may be aqueous or organic in nature. The working electrode is $Cu_2Sb$, but again may comprise any electrically conducting material including those that are active anode materials for Li-ion batteries. The radical generated by the injection of an electron from the working electrode into the initiator species induces the radical polymerization of the vinyl (or derivative) containing monomer species also present in solution. The reduction potential of the initiator species can be tailored to occur within a predefined electrochemical window. The radical generated by this reduction can subsequently induce the polymerization of vinylic containing monomers, independent of the electrochemical reduction potential of the monomer, which may be outside the predefined electrochemical window. Therefore, an electropolymerized coating on the surface of the working electrode containing vinylic containing monomers can be achieved despite that the direct electropolymerization of these species is not possible because their reduction potential is outside the predefined electrochemical window. Also as stated, while water is mentioned as a solvent, it is not the sole solvent from which electrodeposition may be performed.

Since there are numerous vinyl-based functional groups suitable for radical initiated electropolymerization, and a large variety of copolymers possible through co-electrodeposition of multiple monomers, the present method technique can provide final coatings with highly specialized properties, including direct control over such coating characteristics as glass transition temperature, mechanical strength, ionic conductivity, and hydrophobicity. Multiple monomer species in solution may contribute to the properties of the overall electropolymerized film, the resulting properties being accessible by adjusting the monomer concentration. The ratio in which the monomer species is incorporated into the electrodeposited polymer is a function of the corresponding monomer concentration in solution and their polymerization rates.

Monomers having the above-described characteristics that can be controllably introduced into coatings are also desirable for 3D Li-ion electrochemical energy storage cells. Such control is necessary for high Li-ion cell performance and solid polymer electrolyte compatibility with the positive and negative electrodes. It is a requirement for an electrodeposited solid polymer electrolyte to be electrically insulating; therefore, the electropolymerization of such a solid electrolyte onto a working electrode is a self-limiting process. A desirable characteristic of a self-limiting electropolymerization process is that the polymerization continues until the entire surface of the working electrode is coated with a solid polymer that is sufficiently electrically insulating. This allows for a conformal, electrically insulating coating of a complex, 3D structure as a working electrode. For example, a 3D working electrode may include a negative electrode current collector and anode material for a Li-ion cell, and be interdigitated electrode such that the positive electrode is directly coated onto the surface of the solid polymer electrolyte.

Because the solid polymer electrolyte is electropolymerized in a self-limiting manner, the resulting film is of nanoscale thickness, where the solid state transport length of Li-ions is substantially decreased from the current state-of-the-art of approximately 100 microns to a distance below 1 micron. Additionally, because a high surface area 3D electrode is conformally coated with a solid state electrolyte, the active material can be incorporated into the Li-ion cell in such a way that the transport of Li-ions within the electrodes is also reduced to a characteristic distance of approximately a micron, while maintaining a high overall energy density.

A potentiostatic electrochemical deposition method using a voltage corresponding to the reduction of the initiator species may be applied. As mentioned in Section A, multiple potentiostatic pulses should be performed as gas evolution from the electrode surface may occur. When appropriate monomers, defined as monomers that contain a vinyl group or a derivative thereof, in addition to an initiator are included in the deposition solution, the adherence of the gas to the surface of the working electrode may be increased. In addition to the gas formation, permeation of the solvent into the resulting electropolymerized film may occur due to polymer swelling. Because of the gas formation and solvent permeation, the potential used to induce the electropolymerization of the solvated species in the deposition solution should be held constant until the current asymptotically reaches a minimum, non-zero steady state value. It should be noted that the number of cycles to achieve this minimum current and the minimum current value will be a function of the species and their corresponding concentrations in the deposition solution. Optimum values for each should therefore be determined for a specific deposition solution.

In addition to using a non-zero steady state current value as a criterion for which the potential is extinguished, a potentiostatic pulsed deposition procedure may also be employed. A pulsed procedure is based on holding an applied potential, which will have a corresponding deposition current, for a chosen time period. This is defined as the "On" segment of the pulse. After the allotted time, the system is held at a state in which no current is passed between the electrodes for a selected time, which is defined as the "Off" segment of the pulse. The combination of an "On" and an "Off" segment constitutes one complete pulse which is repeated for a predetermined number of pulses. Radicals are produced due to the injection of electrons from the working electrode into the initiator species during the "On" segment of the pulse. During the "Off" segment, radicals are no longer continuously produced, but the polymerization of the appropriate monomers continues through a radical propagation mechanism until the reaction is terminated. The reaction is re-initiated through the generation of radials during another "On" segment of the subsequent pulse.

Appropriate concentrations for initiator species have been discussed in Section A, while concentrations of appropriate monomer species, are also species specific. Typical concentrations may range over three orders of magnitude (approximately 1 mM to about 1 M) while some monomers may require concentrations as high as the solubility limit permits for a given solvent. EXAMPLE 2 describes the aqueous co-electropolymerization of acrylonitrile and methyl acrylate utilizing 4-methoxybenzenediazonium tetrafluoroborate as the initiator, with a $Cu_2Sb$ working electrode. EXAMPLE 2 demonstrates the ability of an initiator species to induce the electropolymerization of vinylic containing monomers on the surface of the working electrode, which otherwise would require reduction potentials significantly more negative. It also demonstrates the ability to co-electropolymerize multiple monomers that when combined exhibit the desired characteristics listed above. Incorporation of acrylonitrile ensures a highly uniform thin film that adheres to the surface of the working electrode, that is electrically insulating, and that can dissolve lithium salts. However, the film lacks the ability to flex with the requisite expansion and contraction of the electrodes which accompany Li-ion intercalation and extraction. Polymeric flexibility improves ionic conduction, and copolymerization of acrylonitrile with a flexible monomer, such as methyl acrylate, can improve the flexibility and allow for higher cycle stability and ionic conductivity through a lowered glass transition temperature.

C. Films Containing Li-ion Salts:

In this embodiment, one of the monomer species containing at least one vinyl derived group is an ionic species which contains $Li^+$ as the cation. The anion portion of the monomer salt is covalently bonded through an additional tethering group to the vinylic group. Solid polymer coatings incorporating an ionic species can be tailored to incorporate the required properties needed for specialized coatings. The specialization is focused on enhancing lithium-ion conductivity of the solid polymer electrolyte for Li-ion cells. There are a large number of vinyl-based functional groups suitable for the incorporation of anion groups, such as sulfonate and carboxy groups, and a variety of tethering groups having various lengths that can bind the anion to the vinyl based group; therefore, the ionic species can also provide the complimentary properties necessary to electropolymerize a solid-polymer electrolyte, functioning both as the medium for which Li-ion ions are transported from the positive and negative electrodes, as well as the medium that electrically isolates the negative and positive electrodes in Li-ion cells. Tethering groups for which the length can be varied as a function of the number of repeat units include: polyethylene oxide, polyethylene glycol, polypropylene glycol, polypropylene oxide, and alkanes, and fluorinated versions thereof. It should be noted that this list is not exhaustive, but the choice of tethering group should not result in an ionic monomer that is insoluble in the deposition solvent, and have a length effective for allowing free motion of the Li-ions. The tethering group length that meets these criteria will vary as a function of structure. As an example, an optimal number of repeat units for a tethering group such as polypropylene glycol should be in the range of approximately 7 to 13. Variation of the number of repeat units allows for a level of control over both the mechanical strength of the electropolymerized film as well as the ionic conductivity. Additionally, the resulting solid-polymer electrolyte electropolymerized in this manner is a single ion conductor because the anion group is bound within the polymer backbone, and thus not mobile when subjected to an external electric field. Single ion conductors have improved Li-ion conductance and higher transference number when compared to solid polymer electrolytes in which the anion is not bound to the polymer backbone.

For non-ionic monomers and the initiator species, the possible concentration ranges as well as the ideal concentration ranges are set forth in Sections A and B hereof, respectively. Concentrations can also vary widely from less than about 1 mM to more than approximately 1 M for the ionic monomer species. With respect to the electropolymerization conditions, the methods described in Section B are also applicable to the present embodiment. A potentiostatic electrochemical deposition method using a voltage that corresponds to the reduction of the initiator species may be utilized in the present embodiment. Multiple potentiostatic cycles may be performed to prevent the accumulation of gas on the working electrode surface which may result from the electrochemical reduction of the initiator species, and which can spatially inhibit the electropolymerization of additional monomer species contained in the deposition solution, resulting in a heterogeneous solid polymer electrolyte containing pinholes or other such defects. Permeation of solvent through the resulting solid polymer electrolyte is also considered in this embodiment. The potential used to induce the electropolymerization of the solvated species is therefore held constant until the current asymptotically reaches a non-zero steady state value for which the value will be a function of the deposition solution composition. The number of potentiostatic cycles and the minimal current value will be a function of the deposition solution composition.

In addition to the electrochemical deposition technique described above, a potentiostatic pulsed deposition procedure as described hereinabove may be employed. Radicals are generated in both methods resulting from a net current being passed through the cell due to the injection of electrons from the working electrode into the initiator species while a potential is applied. When the net current is zero during the "Off" segment of the pulse, radicals are no longer produced. The polymerization of the vinylic containing groups, however, continues through a radical propagation mechanism until the reaction is terminated, being re-initiated when a potential is again applied to the working electrode during a subsequent pulse. There are advantages and disadvantages associated with each electrochemical technique which will be specific to the species contained in the deposition solution. Specific application of this embodiment utilizing 4-methoxybenzenediazonium tetrafluoroborate to initiate the co-electropolymerization of polyacrylonitrile, methyl acrylate, and a sulfopropylacrylate salt utilizing $Cu_2Sb$ as the working electrode is described in EXAMPLE 3.

D. Films having Li-ion Solvating Groups:

The present embodiment is a variation of the embodiment described in Section B, hereof, and includes a deposition solution that comprises at least one vinyl-based group and repeat units of a functional group that solvates Li-ion salts. The incorporation of the Li-ion is through weak bonding of the positively charged Li-ion to negative dipole moments associated with electronegative atoms contained in the repeat unit. Oxygen is an electronegative atom, and examples of repeat units are ethylene oxide and propylene oxide. The distinction between the present embodiment and the embodiment described in Section C is that the anion of the lithium salt is not bound in the polymer backbone. To incorporate Li-ions, and thereby induce Li-ion conductivity, the solid-polymer electrolyte is post soaked in a solution containing an appropriate lithium salt, such as lithium perchlorate and lithium trifluoromethansulfonate, at an appropriate concentration. The solution may be aqueous or organic in nature having various concentrations from on the order of mM to the solubility limit of the salt in the given solvent. The solution includes lithium salts that can be solvated by the electropolymerized solid-polymer electrolyte, and must not induce pinholes or other such defects that could compromise the integrity or otherwise diminish the needed properties of the described electropolymerized solid-polymer electrolyte. Through the incorporation of functional groups having electronegative atoms that can solvate Li-ions, the Li-ion conductivity of the resulting solid polymer coating is increased. Other desirable solid-polymer electrolyte properties may also be introduced into the coating using the post-soaking method.

Similarly, for other monomers utilized in previous embodiments of this invention, the concentrations of the vinylic species described in the present embodiment may vary from less than about 1 mM to more than approximately 1 M. With respect to the electropolymerization conditions, the methods described in the second and third embodiments are also applicable to the embodiment described herein. A potentiostatic electrochemical deposition method having a voltage that corresponds to the reduction of the initiator species may be used in the present embodiment. Multiple potentiostatic cycles may again be used to prevent the accumulation of gas on the electrode surface. Additionally, a potentiostatic pulsed deposition procedure may be employed. Additionally, the embodiments described in Section C and this Section D may be combined to yield a solid polymer electrolyte containing ionic vinylic species having $Li^+$ as the cation and a bound anion as well as vinylic species having electronegative atoms that can subsequently solvate Li-ion salts. EXAMPLE 4, hereof describes characteristic potentiostatic current profiles for the electropolymerization of such solid polymer electrolytes.

E. Functional Solid-Polymer Electrolytes:

Systems, or combinations thereof, resulting in functional solid-state lithium-ion cells utilizing the above teachings to electropolymerize a solid-polymer electrolyte directly on to the surface of $Cu_2Sb$ are discussed below. The first embodiment of this invention relates to the development of novel initiators for the electropolymerization of monomers and oligomers resulting in a viable solid polymer electrolyte. This work is focused on organic halides, such as bromoisobutyronitrile (BrIBN), as wells as diazonium species as the initiator. The reduction potential of BrIBN is ca. $-1.0$ V vs SSCE while the diazonium species are ca. $-0.65$ V vs SSCE. These reduction potentials are important as it is within the electrochemical potential window of the solvent of interest, in this case water. The solid polymer electrolyte films deposited have been characterized using the following coating properties: ionic conductivity as well as film thickness, robustness, uniformity and coverage. With respect to the BrIBN initiated solid polymer electrolyte films, a one hour deposition resulted in film thicknesses in the range of 16±6 microns, and the surface was typically rippled. Upon drying the films or during aggressive rinsing, the films often experienced peeling or delaminating from the electrode surface. This was due to the fact that the BrIBN initiator, and therefore the film, is not known to chemically bond, or graft, to the electrode surface. Films deposited from BrIBN also exhibited very low ionic conductivity at room temperature (RT) for which the value has been measured at $6\pm3\times10^{-8}$ S/cm. While the BrIBN system resulted in functional solid polymer electrolytes the initiator has become focused on diazonium species because of the low ionic conductivity as well as the lack of surface bonding associated with the BrIBN system.

Films deposited utilizing a diazonium salt as the initiator exhibited improved properties when compared to BrIBN initiated films. Films were deposited from similar deposition solutions, with the exception of the initiator. In addition to almost an order of magnitude decrease in initiator concentration, the deposition time was also greatly diminished to 5 minutes, versus 1 hr with an organic halide, while still producing solid polymer electrolyte coatings of similar thicknesses. Deposition times are a guideline, and in general shorter times afford thinner films while longer times afford thicker films. The solid polymer electrolyte coatings electropolymerized using a diazonium initiator also exhibited increased resistance to peeling and delamination. It should be noted, however, that peeling and delamination is observed for coating thicknesses on the order of 10 μm and greater. The films were uniform, defined as coating the entire electrode so that when the second electrode is applied an internal short is not observed, had very smooth surfaces, and exhibited higher ionic conductivities ($6\pm2\times10^{-7}$ S/cm). Another advantage of initiating the electropolymerization using diazonium salts is that the structure of the diazonium initiator has a degree of tunability through modifying the structure for increased ionic conductivity and transference number in addition to being able to tailor the reduction potential of the diazonium initiator.

Tailoring the initiator for structural features including the PEG tail length, position on the benzene ring, and addition of functional groups onto the tail or ring, as examples, the incorporation of a PEG tail having a chosen length onto the initiator allows for tuning of the amount of lithium solvating PEG groups which, in addition to other coating properties, can have a positive change in the ionic conductivity.

Reference will now be made in detail to the present embodiments of the invention, examples of which are illustrated in the accompanying drawings. It will be understood that the FIGURES are presented for the purpose of describing particular embodiments of the invention and are not intended to limit the invention thereto. Turning first to FIG. 1, hereof, structures of solid-polymer electrolyte coatings using an organic halide (non-PEG) initiator and a p-PEG$_{400}$ benzene diazonium tetrafluoroborate initiator, and using the same monomers and monomer concentrations, are illustrated. Without a PEG-based initiator, the ionic conductivity is $6\pm3\times10^{-8}$ S/cm at 25° C., while with a PEG-based initiator the conductivity is $6\pm2\times10^{-7}$ S/cm at 25° C. The position of the tail, whether PEG-based or otherwise, can also be varied between the meta, para, and ortho position to the diazonium group on the benzene ring. The position of the above described group was further investigated to determine if: (1) the position of the tail changed the grafting ability of the initiator, which affects the film adhesion and also the thickness of the resulting solid polymer electrolyte coating; (2) the lithium solvating PEG tail aids the lithium cation migration to the electrode surface. The degree to which the tail can aid the lithium migration to the electrode surface should be a function of the position of the tail on the benzene ring. With the PEG tail in the ortho position, the tail should be directly adjacent and therefore pointed toward the electrode surface; thereby allowing for better lithium cation migration at the electrode surface. Further, the tail in the ortho position would sterically hinder further initiator reactions at the surface when compared to the para and/or meta positions. This could result in a decrease in the grafting density of the solid polymer electrolyte coating thereby decreasing film adhesion; and (3) the reduction potential of the initiator could be tuned.

Ortho-positioned tails, regardless of length, were found to afford poorly grafted solid polymer electrolyte coatings resulting in films that delaminated during drying or other such post-processing. With the tail in the meta position, the initiator worked poorly, if at all, and no films were observed, while with the tail in the para position, films adhered better to the electrode surface and much of the delamination issue observed with the ortho initiators were decreased, but not overcome entirely. Theoretically, the diazonium-based initiators may be mixed together in a co-initiator system, allowing for good grafting to the electrode surface and good lithium migration at the electrode surface. This embodiment then also includes, but is not be limited to, mixing one or more initiators as a method of tuning the initiators. The above described changes did not result in significant changes in the reduction potential of the diazonium species.

Another variation in the diazonium salt structure includes the addition of a functional group to the molecule. The addition of an anion group to the end of the tail, is now discussed, but the present invention should not be limited thereto. A functional group could also be incorporated onto the benzene ring or elsewhere on the tail, and the teaching can encompass other functional groups in locations other than at the end of the tail. Other possible functional groups include but are not limited to: aromatic and aliphatic hydrocarbons, cations, amines, thiols, alcohols, and diazonium salts. The inclusion of a functional group onto the tail include increasing the ionic conductivity and transference number of the separator material. By incorporating a fixed anion site onto the tail, lithium cations are brought closer to the electrode surface, which could increase the ionic conductivity of the separator. Second, the fixed anion site will increase the transference number as only lithium cations are able to migrate. Illustrations of the various diazonium based structures investigated are containing in FIG. 1.

Advantages of using a diazonium salt as the initiator are many, but there are also some technical hurdles. As mentioned above, an undesirable percentage of the solid polymer electrolyte coatings that were greater than 10 µm thick had a propensity to delaminate from the Cu$_2$Sb surface. A second difficulty to overcome was the auto-polymerization that diazonium salts can undergo when exposed to a surface that can be oxidized through the donation of an electron to the diazonium species. Auto-polymerization is observed, to varying degrees and rates based on the structure of the diazonium species, once the Cu$_2$Sb based working electrode is submersed in the electropolymerization solution, and occurs without a potential being applied, thereby removing a degree of the control electropolymerization techniques afford. The uncontrolled reaction resulted in solid polymer electrolyte coating thicknesses that were undesirable, that is greater than 10 microns, which delaminated easily. Controlling the auto-polymerization through structural changes to the initiator, which would shift the reduction potential, were unsuccessful. The amount or rate of auto-polymerization was changed, but never completely eliminated. A method for avoiding the auto-polymerization is detailed below.

F. Monomer Progress:

An embodiment of this invention relates to the sequential development of a novel co-polymerization utilizing the above described initiators that affords robust films with a high ionic conductivity and transference number at room temperature. The first step was the incorporation of a crosslinking agent to increase stability of the polymer films and to minimize the degree of crystallinity, or structural order, within the solid polymer electrolyte coating. This is important as it is known that the degree of crystallinity is inversely proportional to the measured ionic conductivity of said solid polymer electrolyte. While in the below described examples, the crosslinking agent is poly(ethylene glycol) diacrylate (PEGDA), any crosslinking agent would suffice assuming the meet the above described criteria. PEGDA is used in this teaching because it is a PEG containing cross-linker and PEG is a good lithium solvating repeating unit. Additionally, crosslinking also increases chemical and mechanical stability which facilitates the addition of a second electrode to complete the lithium-ion cell while simultaneously minimizing the occurrence of internal shorting through the solid polymer electrolyte coating.

Incorporation of a crosslinking agent was shown to be advantageous when comparing acrylic acid based co-electropolymerizations without a crosslinking agent to co-electropolymerizations of acrylic acid with PEGDA (Mn=700). Incorporating a second, non-crosslinking monomer, such as poly(ethylene glycol) methyl ether acrylate (PEGMEA, Mn=480 g/mol), did not provide the desired mechanical properties and chemical resistivity nor did it reduce the crystallinity of the resulting solid polymer electrolyte coating. This was due to a lack of crosslinking agent in the electropolymerization solution. By incorporating PEGDA into the electropolymerization solution, and therefore the film, the chemical resistance is increased and functional solid polymer electrolyte coatings were observed. The degree of chemical resistivity is such that attempts to redissolve the solid polymer electrolyte coating off the surface of the working electrode, in this case $Cu_2Sb$, were unsuccessful in a range of solvents, even under sonication.

The incorporation of a lithium-ion monomer salt also had a beneficial effect on the ionic conductivity of the above described electropolymerized solid polymer electrolyte coatings. A common shortcoming for solid polymer electrolyte separator materials is a low transference number, which is defined as the fraction of the observed ionic conductivity that can be attributed to the movement of the ion of interest, in this case the lithium cation. With a low transference number, a large portion of the ionic conductivity can be attributed to the movement of anion or other such species that do not contribute to the reactions which electrochemically store energy. A typical solid polymer electrolyte based separator has a transference number of 0.1-0.3, meaning only 10-30% of the observed conductance is due to the movement of lithium cations through the electrolyte. By incorporating an anionic monomer that is immobilized in the polymer matrix, as described in the above embodiments, a transference number of greater than 0.5 has been demonstrated in the above described electropolymerized solid polymer electrolyte coating.

G. Electropolymerization Cell and Electrochemical Method:

As discussed hereinabove, an observed complication when using diazonium-based initiators is auto-polymerization. The auto-polymerization process is less controllable and also induces an undesirable chemical change at the surface of the working electrode. While the prior art describes this phenomenon in detail, the focus in the prior art is how to productively utilize the auto-polymerization process, not necessarily how to overcome or circumvent it. Diazonium salts degrade in aqueous solutions and the rate of the degradation is a function of the solution pH. This degradation can be catalyzed by metallic surfaces through an electrochemical reduction reaction where a metallic species of the working electrode donates an electron to the diazonium species thereby initiating the reduction. As $Cu_2Sb$ contains a transition metal that can donate an electron, that is copper, the auto-polymerization reaction is observed upon submersing the $Cu_2Sb$ electrode into the electropolymerization deposition bath. While $Cu_2Sb$ is the working electrode material described throughout this document, it is well known that other metallic surfaces also cause auto-polymerization of the diazonium species. The auto-polymerization causes poor film adhesion to the substrate which increases delamination. Due to the lack of a strong bond between the electrode surface and the solid polymer electrolyte, deposition solution continues to be transported to the electrode surface; thereby resulting in thick films that are less robust. The combination of thicker solid polymer electrolyte coatings with a decrease in adhesion strength results in a decrease in the success rate associated with the application of the second electrode. This, as discussed previously, is due to an internal short through the electropolymerized solid polymer electrolyte. The electropolymerization deposition method as described results in a functioning solid-state lithium-ion cells approximately 65% of the time.

In order to prevent the uncontrolled auto-polymerization onto the surface of the working electrode of interest, the electrochemical cell and the electrochemical method were modified. The principle behind these modifications is to ensure that a potential is applied to the working electrode of interest before coming into contact with the electropolymerization deposition solution so that any electrons that are donated to the diazonium species to facilitate reduction and the rest of the polymerization process is provided by the external source of current, not through the oxidation of a metallic species on the working electrode surface. To accomplish this, a conductive material that is in direct electrical contact with the working electrode of interest is submersed into the electropolymerization deposition solution before submersing the working electrode of interest. A potential is then applied to the working electrode, and by proxy since they are in direct electrical contact, the conductive material submersed in the electropolymerization solution. After the potential is applied, the working electrode of interest is then submersed into the electropolymerization solution. A constraint set upon this conductive material which is submersed into the deposition solution prior to the working electrode of interest is that it must be electrically conducting. Ideally, this material would not induce the auto-polymerization effect as described above. This could possibly be accomplished through inert materials such as platinum or vitreous carbon. However, reactive materials such as copper, could also be utilized with the knowledge that deposition constituents will be consumed. This consumption, however, could be minimized by making the conductive material have a geometry with an extremely small surface area, such as a small diameter wire. In the above described case, that is the working electrode surface of interest having an applied potential before and during submersion into the electropolymerization deposition solution and therefore no auto-polymerization could occur, film thickness decreased over 50%. Furthermore, all peeling/delaminating issues were eliminated using this deposition technique. Lastly, cathode slurry integration was successful over 90% of the samples. This can be attributed to the stronger bond between the polymer coating and the surface of the working electrode as well as the fact that none of the working electrode of interest was consumed during the auto-polymerization process.

Once the solid electrolyte has been demonstrated to conformally coat the electrode material, the complimentary electrode is incorporated in order to complete the Li-ion electrochemical energy storage cell. The final embodiment of the invention described herein is an aqueous based slurry composition that allows the positive electrode to be applied to the surface of the electropolymerized solid polymer electrolyte without inducing damage. As described above, damage is defined as defects or pinholes in the electrically insulating but ionically conducting solid polymer electrolyte. This embodiment utilizes an aqueous based slurry because water has been identified as a solvent that does not induce damage to the solid polymer electrolyte. The cathode material, defined as a substance that is electrochemically active and can store charge through the incorporation and extrusion of Li-ions, is added to the slurry in particulate form. Examples of such cathode materials are $LiFePO_4$, $LiCoO_2$, $LiMnO_2$, and $LiNi_{0.4}Co_{0.2}Mn_{1.4}O_4$. In addition to the cathode material, a polymer binder that is soluble in water and can also be induced to facilitate Li-ion transport within the electrode is also incorporated into the slurry. Potential water soluble polymers can be polyethylene oxide, polyethylene glycol, polypropylene glycol, and polypropylene oxide of varying molecular weights as well as alcohol based polymers and copolymers. It should be noted that this list is not exhaustive and that the criteria that should be met is that the polymer is water soluble and can be induced to transport Li-ions in the solid state within the structure of the positive electrode. In order to induce Li-ion transport in the water soluble polymer, a lithium containing salt can be added. Some examples of salts that can be utilized to induce lithium-ion transport are lithium perchlorate and lithium trifluoromethanesulfonate. The concentration of the salt should be approximately 0.125 mole fraction when using the molecular weight of the repeat unit. In addition to Li-ion salts, Li-ion conducting glass ceramics (LIC-GC) can also be added to the slurry in the form of particulates to enhance Li-ion conductivity throughout the electrode. As a guide, each constituent concentration in terms of mass percent is contained in TABLE 1.

TABLE 1

| | |
|---|---|
| Active material | 50-93% by mass |
| Water soluble polymer binder | 5-30% by mass |
| Lithium-ion salt | 1-12% by mass |
| Conductive ceramic | 1-8% by mass |
| Conducting graphite | 1-8% by mass |
| Acid | 0.1-1% by mass |

Specific application of this embodiment is contained in EXAMPLE 5.

Having generally described the invention, the following EXAMPLES provide greater detail.

EXAMPLE 1

Figure 2:
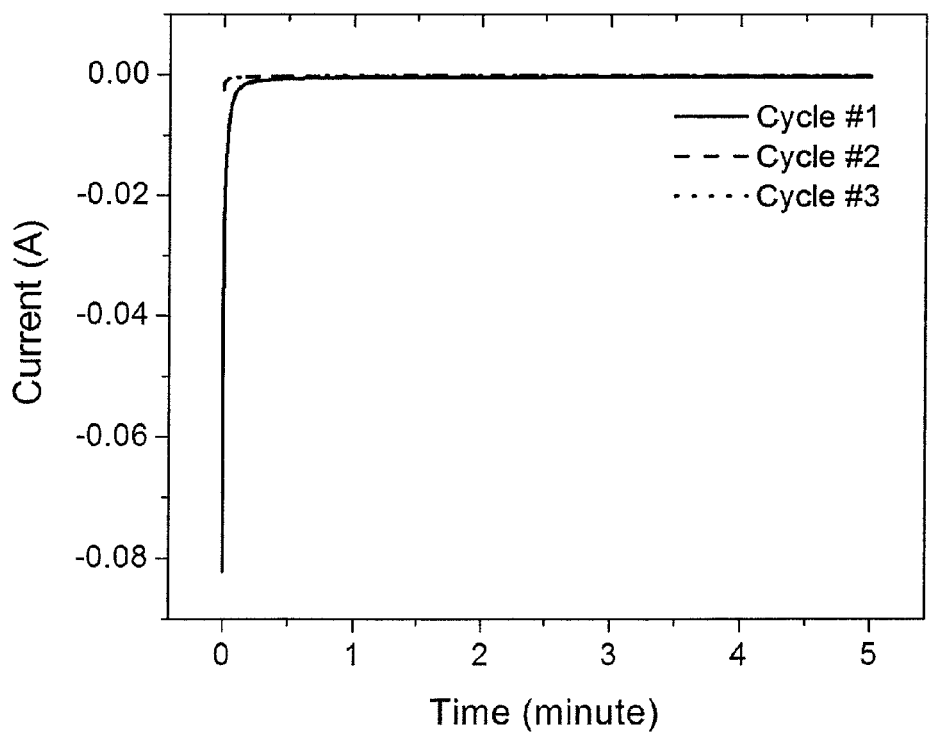
FIG. 2 illustrates chronoamperometry data collected from the three 300 s potentiostatic pulses at −0.65 V vs. Ag/AgCl applied to a $Cu_2Sb$ deposition substrate when submersed in an aqueous electropolymerization solution containing of 0.1 M sulfuric acid, 0.1 M $LiClO_4$, and 0.005 M 4-methoxybenzenediazonium tetrafluoroborate.

To demonstrate the use of an initiator species which can chemically bond to the surface of a working electrode to promote further electropolymerization, copper antimonide ($Cu_2Sb$), which is a known negative electrode lithium intercalation material, was electrochemically deposited onto a copper foil substrate according to a known procedure. The substrate consisting of electrodeposited $Cu_2Sb$ is then placed into a 5% by volume $HNO_3$ cleaning solution for approximately 5 s to remove surface oxides. It is subsequently submersed into an aqueous deposition solution consisting of 0.1 M sulfuric acid, 0.1 M $LiClO_4$ (which acts as the supporting electrolyte), and 0.005 M 4-methoxybenzenediazonium tetrafluoroborate. Dissolved $O_2$ (g) was removed by bubbling $N_2$ (g) through the aqueous solution prior to deposition. The diazonium species is electropolymerized by applying a deposition voltage of −0.65 V vs. Ag/AgCl. Three 300 s potentiostatic pulses were applied sequentially to the deposition substrate. The current profile resulting from these potentiostatic pulses are illustrated in FIG. 2. As demonstrated by the figure, the current magnitude decreases as a function of time for a given pulse. Additionally, the initial current decreases as a function of pulse number. This occurs because the conducting $Cu_2Sb$ surface is being coated with an insulating layer consisting of the reduced 4-methoxybenzenediazonium tetrafluoroborate species.

Figure 3:
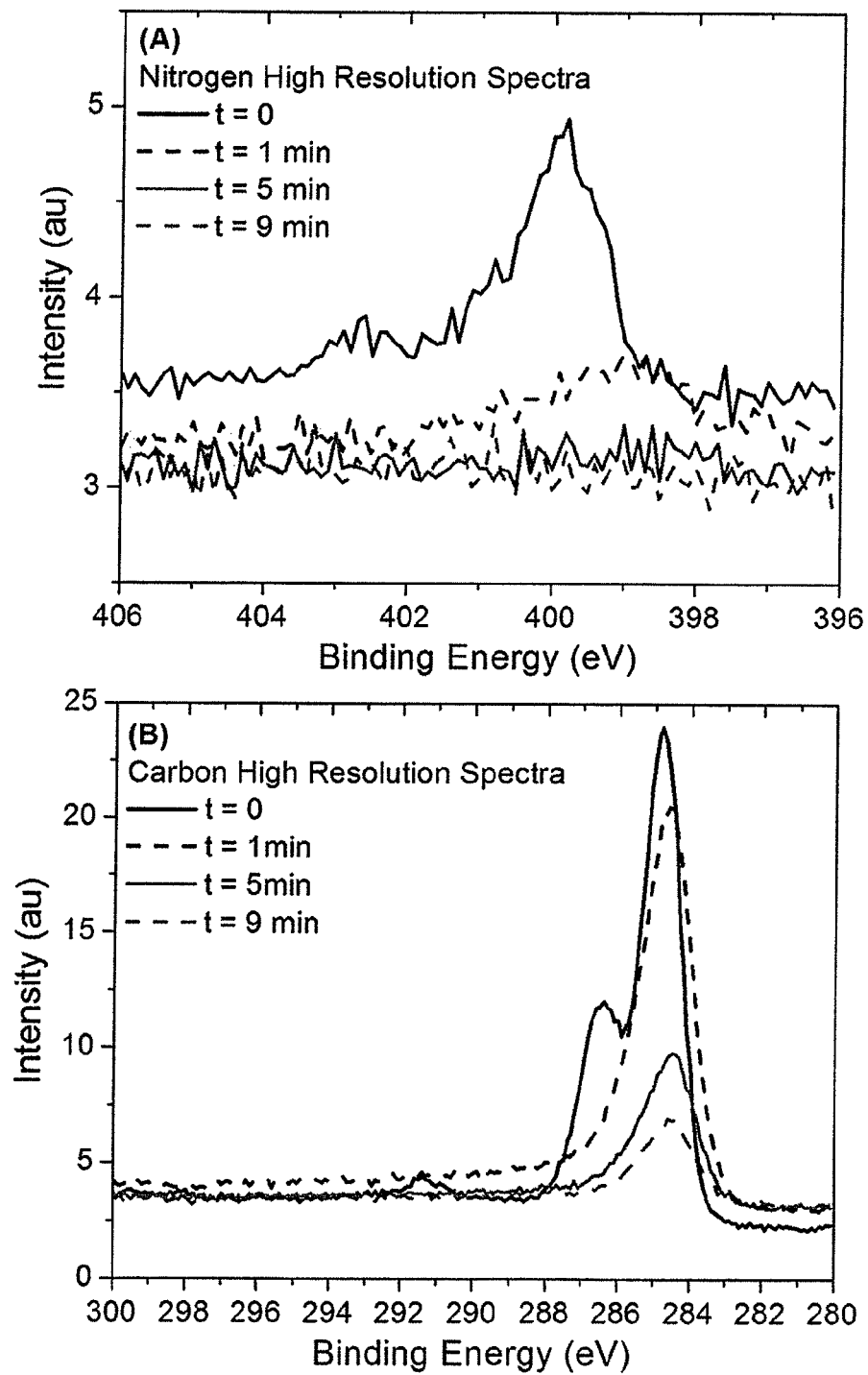
FIG. 3 shows high resolution X-ray photoelectron spectroscopy data collected for the binding energies associated with the nitrogen 1s electron and the carbon 1s electron for varying times of ion sputtering.

To confirm the presence of the diazonium species that is chemically bonded to the surface of $Cu_2Sb$, an X-ray photoelectron spectroscopy (XPS) analysis of the electrode was conducted. This technique is uniquely suited for this analysis because XPS is a surface sensitive technique. Thus, if the diazonium based coating is present, photoelectrons generated from the coated sample due to the bombardment of X-rays will behave differently when compared to an uncoated sample. The preliminary XPS data suggests that a film consisting of a completely reduced diazonium species is not obtained on the surface of the $Cu_2Sb$ substrate. The mechanism which would result in a reduced diazonium species requires the diazonium molecule to release a mole of nitrogen gas per mole of diazonium species upon reduction due to injection of an electron from the working electrode. This process would result in a metal-carbon bond at the carbon site that is para to the methoxy group in the phenyl ring. Based on this mechanism, there should be no nitrogen visible in our XPS data. In the first survey scan, however, nitrogen was observed. Upon further investigation, multiple peaks were de-convoluted with a high resolution scan of the binding energy range associated with the N1s electron, as illustrated in FIG. 3A. The peak at lower binding energy is associated with a nitrogen bond to the surface of the working electrode, i.e. $Cu_2Sb$. That peak is still visible after 1 min of sputtering while the other peaks have either completely disappeared or decreased significantly in intensity. This is consistent with a species that has a strong bond to the surface of the substrate making it sputter at a slower rate. It is possible that after the substrate is submersed in the deposition solution, before a potential is applied to the working electrode, the diazonium species is reacting with the surface to form a bond with a nitrogen bridge.

In addition to a nitrogen bridge there is also evidence of a carbon bond to the surface of the $Cu_2Sb$. This is illustrated in the high resolution spectra, contained in FIG. 3(B) of the binding energy range associated with the C1s electron. After sputtering for 9 minutes, carbon is still observed in the spectrum. This is in contrast to a bare $Cu_2Sb$ electrode where advantageous carbon physisorbed to the surface of the $Cu_2Sb$ is removed with sputtering times on the order of 1 minute. The difficultly associated with removing the carbon from the surface is evidence of a strong metal-carbon bond. Additionally, this chemical bond to the surface follows the mechanism proposed above that the nitrogen is cleaved from the diazonium species allowing the carbon para to the methoxy group to bond to the surface. Release of gas from the $Cu_2Sb$ surface, which is also consistent with the grafting mechanism, is observed during the electrodeposition of the diazonium species.

EXAMPLE 2

In the utilization of the covalently bonded species described Section A to induce the radical polymerization and subsequent grafting of additional monomer species in solution, cyclic voltammetry is employed to identify the reductive polymerization potentials of 4-methoxybenzenediazonium tetrafluoroborate, acrylonitrile, and methyl acrylate. Using this data, the copolymerization of the species is performed on the surface of $Cu_2Sb$ at a potential that reduces the diazonium species, but does not directly reduce the acrylonitrile or methyl acrylate monomers. Subsequent analyses of the deposited films demonstrate the incorporation of all three species in solution; thereby demonstrating the above stated embodiment.

To quantify the potentials at which each of the three species are reduced, cyclic voltammograms (CV) were collected in an $N_2$ (g) glove box with $O_2$ (g) and $H_2O$ levels below 0.1 ppm utilizing anhydrous tetrahydrofuran (THF) with 0.1 M tetrabutylammonium perchlorate (TBAP) as the supporting electrolyte. The working electrode was a glassy carbon disk with a surface area of approximately 0.071 $cm^2$. This system was chosen to provide a sufficiently wide electrochemical window to demonstrate voltages at which the relevant reductions occur. A 0.01 M $Ag/AgNO_3$ non-aqueous reference electrode was utilized in these measurements and the reversible electrochemistry of the ferrocene/ferrocenium couple was used as an internal standard.

Figure 4:
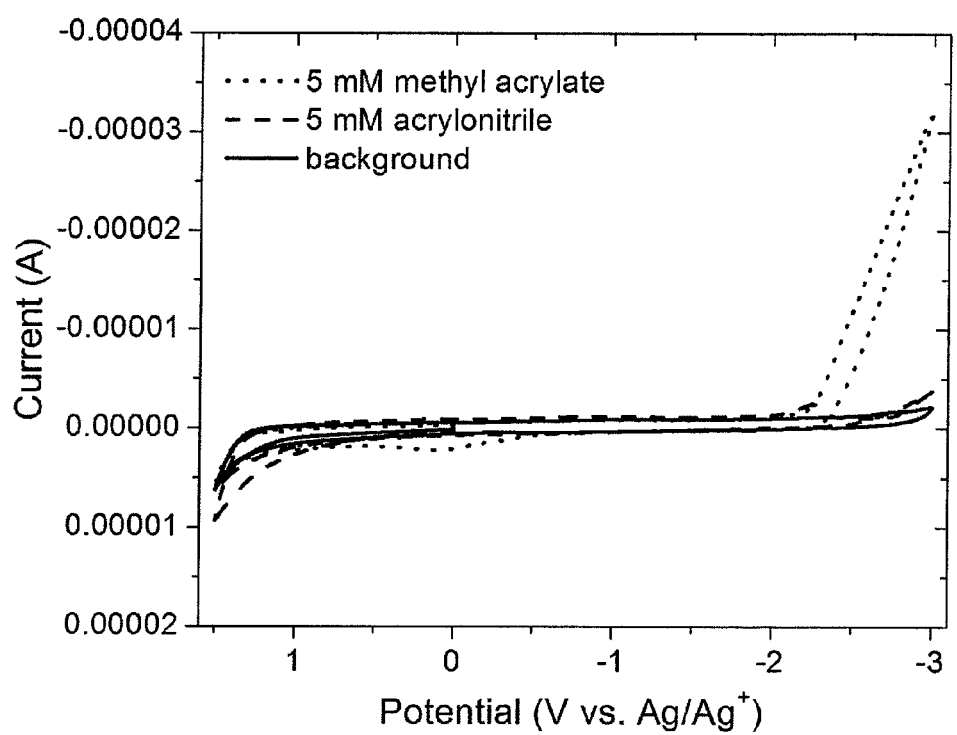
FIG. 4 shows cyclic voltammetry data of the as described electrolyte solution as well as the solution with either 5 mM methyl acrylate or 5 mM acrylonitrile and demonstrates that the direct reduction of methyl acrylate and acrylonitrile cannot be accomplished in a solvent such as water due to solvent reduction.
Figure 5:
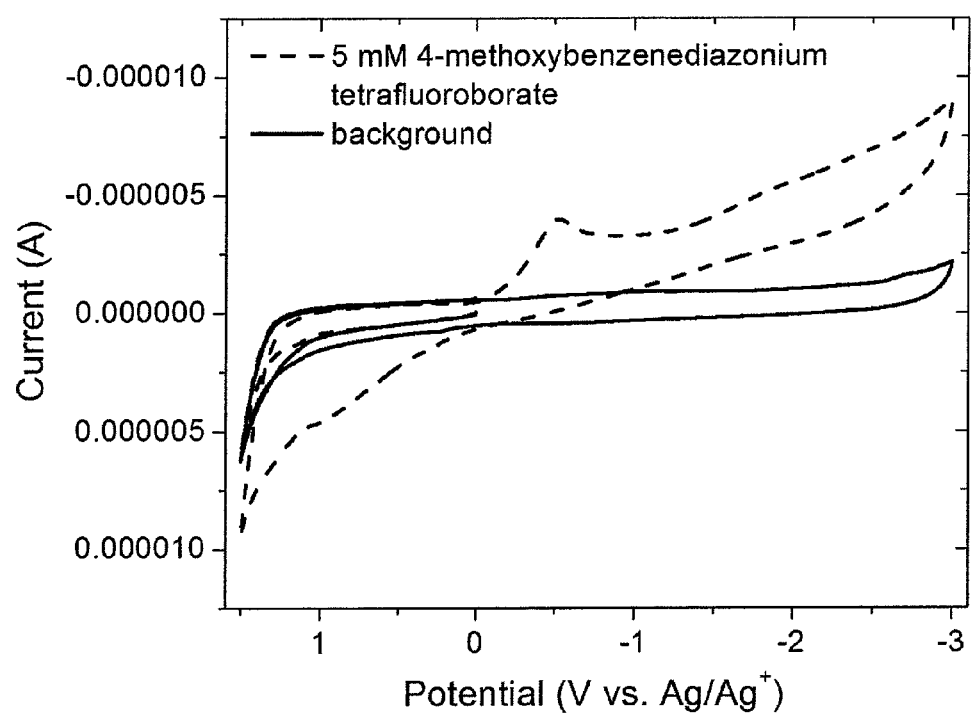
FIG. 5 shows cyclic voltammetry data of the as described electrolyte solution as well as the solution with 0.005 M 4-methoxybenzenediazonium tetrafluoroborate, demonstrating the ability of the diazonium based species to be reduced at more positive potentials than the electrochemical reduction of water.

A scan rate of 0.05 V/s was used for each CV with a positive and negative voltage limit of 1.5 and −3 V vs. $Ag/Ag^+$, respectively. FIG. 4 shows CV of the electrolyte solution (background), the electrolyte solution with 5 mM methyl acrylate, and the electrolyte solution with 5 mM acrylonitrile. The background CV demonstrates that there is no significant electrochemical activity due to the solvent or supporting electrolyte occurring in the potentials scanned in the CV. The methyl acrylate and acrylonitrile solutions, however, undergo electrochemical reductions at approximately −2.1 and −1.9 V vs. Ag/Ag$^+$, respectively. As detailed in the embodiment, these potentials are too negative to directly electropolymerize methyl acrylate and acrylonitrile onto the surface of $Cu_2Sb$ from an aqueous deposition solution. To promote the polymerization of these two monomers at a potential that falls within the desired range, 4-methoxybenzenediazonium tetrafluoroborate, the species that has been demonstrated in example 1 to chemically bond to the surface of $Cu_2Sb$, is utilized. FIG. 5 shows CV of the electrolyte solution and the electrolyte solution with 5 mM 4-methoxybenzenediazonium tetrafluoroborate. Based on the data plotted in the figure, it is clear that the diazonium species undergoes an electrochemical reduction at approximately −0.5 V vs. Ag/Ag$^+$, which is within the acceptable potential range when electropolymerizing onto the surface of a $Cu_2Sb$ substrate.

To demonstrate that the copolymerization of methyl acrylate and acrylonitrile can occur at a potential that is not associated with the direct reduction of the monomer through an initiator species on the surface of $Cu_2S$, reflectance infrared (IR) will be used. Reflectance IR was chosen because it is an excellent technique that can identify the presence or absence of polymers or copolymers formed when electropolymerizing from solutions containing one or multiple monomers. IR spectroscopy measures active vibrational modes that can be used to identify components in the film. Because the constituents associated with both methyl acrylate and acrylonitrile are IR active, characteristic absorptions can be used to confirm the presence of each component in the film; thereby demonstrating the co-electropolymerization.

Figure 6:
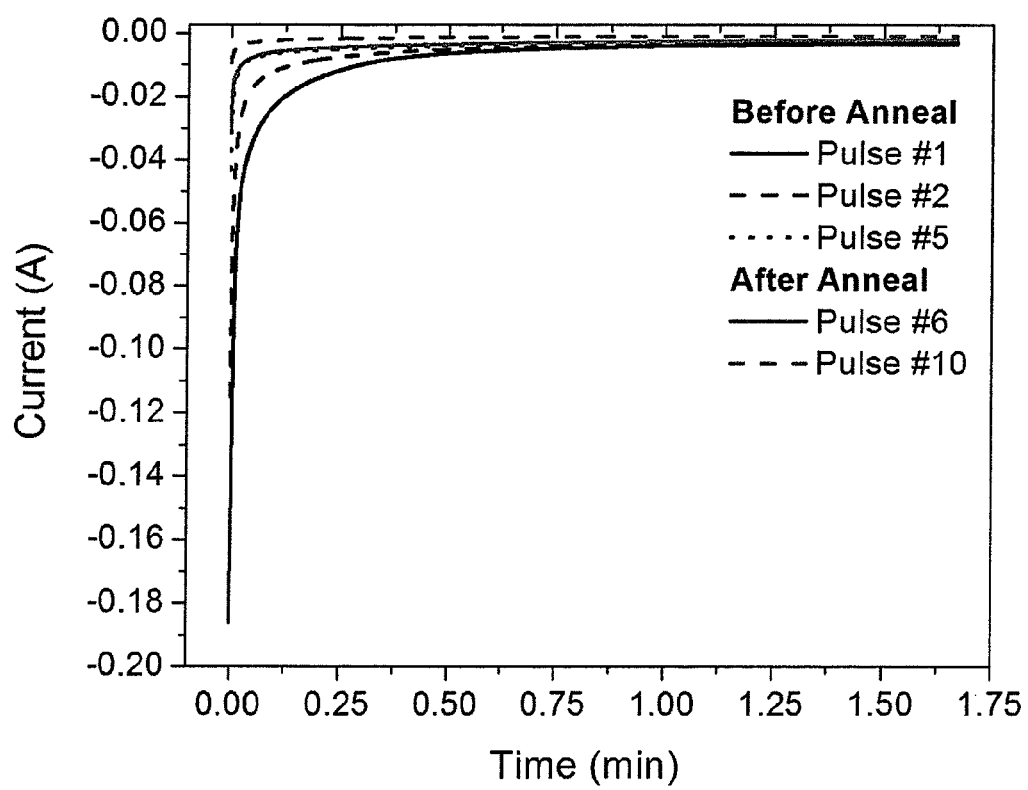
FIG. 6 shows chronoamperometry data collected from the five 100 second potentiostatic pulses at −0.65 V vs. Ag/AgCl applied to a $Cu_2Sb$ deposition substrate when submersed in an aqueous electropolymerization solution containing of 0.1 M sulfuric acid, 0.1 M $LiClO_4$, 0.005 M 4-methoxybenzenediazonium tetrafluoroborate, 0.4 M acrylonitrile, and 0.3 M methyl acrylate.

To prepare the samples, a substrate consisting of electrodeposited $Cu_2Sb$ is placed into a 5% by volume $HNO_3$ cleaning solution for approximately 5 s to remove surface oxides. It is subsequently submersed into an aqueous deposition solution consisting of 0.1 M sulfuric acid, 0.1 M $LiClO_4$ (which acts as the supporting electrolyte), and 0.005 M 4-methoxybenzenediazonium tetrafluoroborate. Dissolved $O_2$ (g) was removed by bubbling $N_2$ (g) through the aqueous solution. 0.4 M acrylonitrile was then added to the deposition and stirred thoroughly to ensure complete dissolution of the monomer. 0.3 M methyl acrylate was then added and also stirred thoroughly. The co-electropolymerization is induced by applying a potential of −0.65 V vs. Ag/AgCl for five, 100 s potentiostatic pulses. Gas bubbles formed during the reduction of the 4-methoxybenzenediazonium tetrafluoroborate were removed between each pulse from the deposition substrate surface by removing and then subsequently re-submersing the substrate in the solution until the gas was completely removed. The current profile resulting from these potentiostatic pulses are contained in FIG. 6. As demonstrated by the figure the current magnitude decreases as a function of time for a given pulse. Additionally, the initial current decreases as a function of pulse number. This is occurring because the conducting $Cu_2Sb$ surface is being coated with an insulating layer consisting of the co-polymer. While the current response is similar to that observed for the electrodeposition of the diazonium based species, it should also be noted that the films are visually much thicker when compared to the films described in EXAMPLE 1. After completion of the five pulses, the samples were placed into a vacuum at 100° C. for 1 h at approximately −25 mmHg. After the hour at 100° C., the samples were allowed to cool to room temperature before removing them from vacuum. This process was repeated to achieve the final copolymer film.

Figure 7:
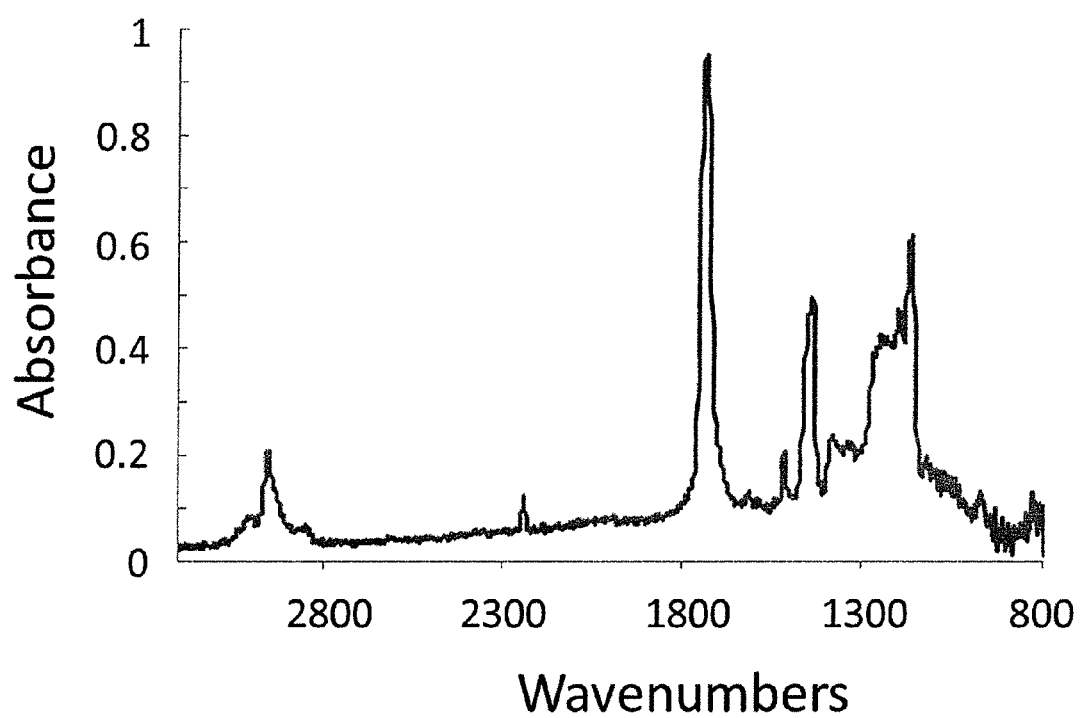
FIG. 7 shows a characteristic reflectance IR spectrum collected from a solid polymer electrolyte coating confirming the presence of both acrylonitrile and methyl acrylate, the two monomer constituents being dissolved in the electropolymerization deposition solution.

To confirm the presence of the acrylonitrile and methyl acrylate, reflectance IR spectra were collected from samples prepared using the above mentioned procedure. FIG. 7 shows a representative reflectance IR spectrum for a 10 μm spot of the methyl acrylate-acrylonitrile copolymer electropolymerized onto the surface of a $Cu_2Sb$ substrate. IR peaks characteristic of each monomer can be seen in the final polymer. The peak at 2241 cm$^{-1}$ is characteristic of a nitrile group and thus is evidence that acrylonitrile is incorporated into the electropolymerized film. Additionally, the peak at 1731 cm$^{-1}$ is characteristic of an ester carbonyl which is indicative of methyl acrylate. These two peaks therefore demonstrate that the final electrodeposited film contained both of the monomer constituents. This data confirms the ability of the initiator species to induce the reductive electropolymerization of multiple species in solution at a potential more positive than that required for direct electropolymerization.

EXAMPLE 3

To demonstrate inducing ionic conductivity by incorporating an ionic monomer containing Li$^+$ as the cation and an anion bound to the vinylic group through a tethering group, the copolymerization of acrylonitrile, methyl acrylate, and sulfopropylacrylate salt was conducted similarly to that described in EXAMPLE 2 using 4-methoxybenzenediazonium tetrafluoroborate. The concentration of the species that induces ionic conductivity, sulfopropylacrylate salt, was varied and the ionic conductivity was monitored using electrochemical impedance spectroscopy (EIS). To prepare the samples, a substrate consisting of electrodeposited $Cu_2Sb$ is placed into a 5% by volume $HNO_3$ cleaning solution for approximately 5 s to remove surface oxides. It is subsequently submersed into an aqueous deposition solution consisting of 0.1 M sulfuric acid, 0.1 M $LiClO_4$ (which acts as the supporting electrolyte), and 0.005 M 4-methoxybenzenediazonium tetrafluoroborate. Dissolved $O_2$ (g) was removed by bubbling $N_2$ (g) through the aqueous solution. 0.4 M acrylonitrile was then added to the deposition and stirred thoroughly to ensure complete dissolution of the monomer. 0.3 M methyl acrylate was then added and also stirred thoroughly. The sulfopropylacrylate salt was then added to the deposition solution. The concentration of the sulfopropylacrylate salt was varied and the concentration of the salt for each co-electropolymerization deposition solution is contained in TABLE 2.

Figure 8:
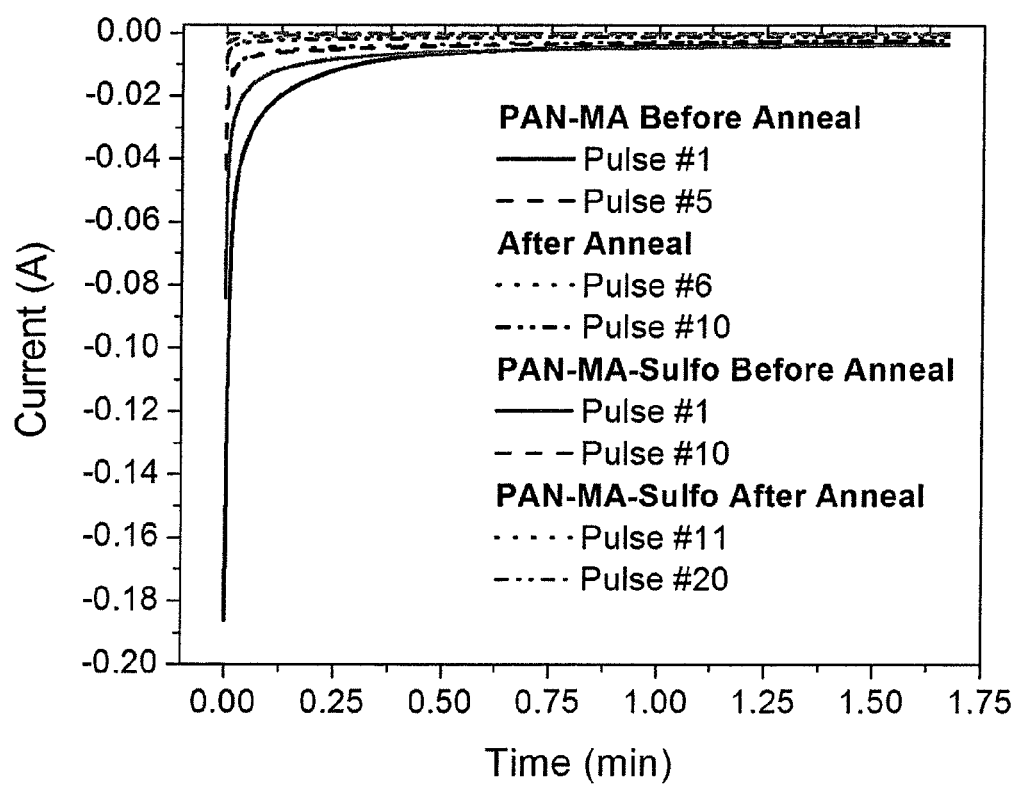
FIG. 8 shows selected chronoamperometry curves collected from a characteristic electropolymerization procedure consisting of ten, 100 s potentiostatic pulses at −0.65 V vs. Ag/AgCl applied to a $Cu_2Sb$ deposition substrate when submersed in an aqueous electropolymerization solution containing of 0.1 M sulfuric acid, 0.1 M $LiClO_4$, 0.005 M 4-methoxybenzenediazonium tetrafluoroborate, 0.4 M acrylonitrile, 0.3 M methyl acrylate, and sulfopropylacrylate salt having various concentrations.

The co-electropolymerization is induced by applying a potential of −0.65 V vs. Ag/AgCl for ten, 100 s potentiostatic pulses. Gas bubbles formed during the reduction of the 4-methoxybenzenediazonium tetrafluoroborate were removed between each pulse from the deposition substrate surface by removing and then subsequently re-submersing the substrate in the solution until the gas was completely removed. After completion of the ten electropolymerization pulses, the samples were placed into a vacuum oven at 100° C. for 1 h at approximately −25 mmHg. After the hour at 100° C., the samples were allowed to cool to room temperature before removing them from vacuum. This process was repeated to achieve the final copolymer film. The current profile resulting from these potentiostatic pulses with and without sulfopropylacrylate salt in the deposition solution are contained in FIG. 8. As demonstrated by the figure the current magnitude decreases as a function of time for a given pulse. Additionally, the initial current decreases as a function of pulse number.

This is occurring because the conducting $Cu_2Sb$ surface is being coated with an insulating layer consisting of the co-polymer. The current response is similar to that observed for the electrodeposition of the polymer film described in EXAMPLE 2. Additionally, the visual appearance of the film is comparable to that described in EXAMPLE 2.

TABLE 2

Co-electropolymerization of acrylonitrile (0.4M), methyl acrylate (0.3M), and sulfopropylacrylate salt.

| Sample # | sulfopropylacrylate salt M | Ionic Conductivity S/cm |
|---|---|---|
| PAN-MA-1 | 0 | BDL |
| PAN-MA-2 | 0.001 | BDL |
| PAN-MA-3 | 0.002 | BDL |
| PAN-MA-4 | 0.011 | BDL |
| PAN-MA-5 | 0.016 | $1 \times 10^{-10}$ |
| PAN-MA-6 | 0.022 | $1 \times 10^{-9}$ |
| PAN-MA-7 | 0.043 | $4 \times 10^{-8}$ |

Figure 9:
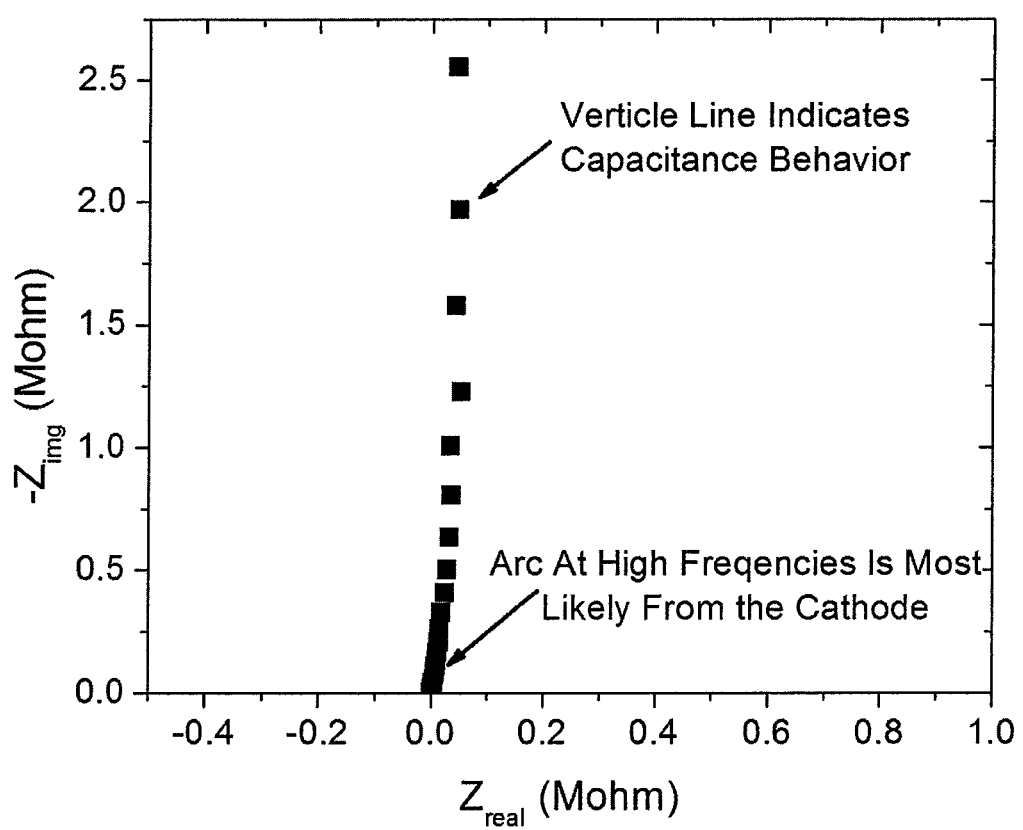
FIG. 9 shows a characteristic Nyquist plot generated from electrochemical impedance spectroscopy data of a solid polymer electrolyte coating electropolymerized onto the surface of $Cu_2Sb$ without including sulfopropylacrylate salt in the electropolymerization deposition solution.
Figure 10:
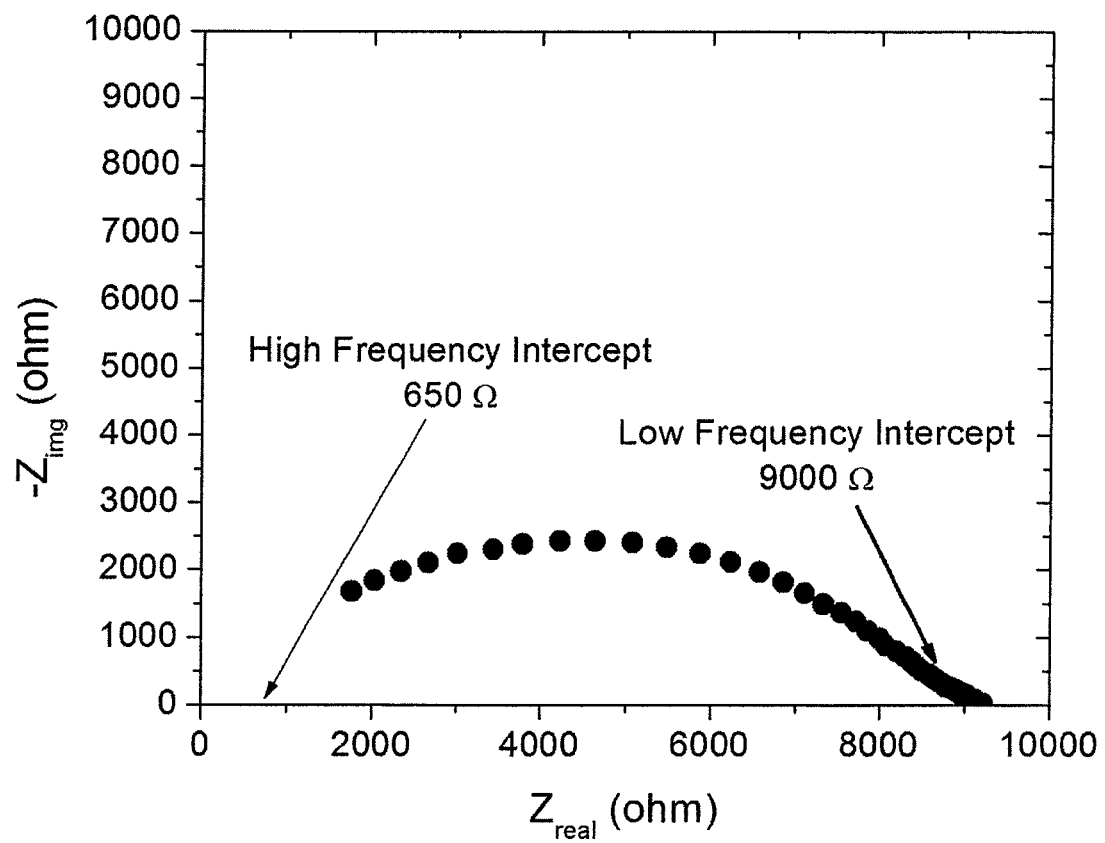
FIG. 10 shows a characteristic Nyquist plot generated from electrochemical impedance spectroscopy data of a solid polymer electrolyte coating electropolymerized onto the surface of $Cu_2Sb$ which included sulfopropylacrylate salt in the electropolymerization deposition solution and demonstrates the impact on ionic conductivity, and thus the functionality of the polymer coating, that the sulfopropylacrylate salt induces.

To quantify the effect of the sulfopropylacrylate salt on the ionic conductivity of the electropolymerized film, the concentration was varied from 0 M to 0.043 M. A characteristic EIS spectrum of a sample that contained 0 M sulfopropylacrylate salt is contained in FIG. 9. As illustrated by the figure, the film is not ionically conductive and behaves more like a dielectric. The dielectric behavior of the film results in the characteristic capacitor response shown in FIG. 9. Once the concentration of the sulfopropylacrylate salt is increased, however, a significant increase in ionic conductivity is observed. This is clearly demonstrated in the characteristic EIS spectrum contained in FIG. 10 from an electropolymerized coating for which the deposition solution contained 0.043 M sulfopropylacrylate salt. Based on the high frequency intercept, the calculated ionic conductivity of the co-electropolymerized film is $4 \times 10^{-8}$ S/cm. The effect of the sulfopropylacrylate salt concentration in the deposition on the ionic conductivity of the resulting film is quantified in TABLE 2. As demonstrated by TABLE 2, the higher the sulfopropylacrylate salt concentration, the higher the measured ionic conductivity.

EXAMPLE 4

To demonstrate inducing ionic conductivity by incorporating a monomer containing at least one vinylic group that also has the ability to solvate Li-ion salts through a repeat unit containing an electronegative element, the copolymerization of acrylonitrile, methyl acrylate, and poly(ethylene) glycol methyl ether methacrylate was conducted in a similar manner to that described in EXAMPLE 2 using 4-methoxybenzenediazonium tetrafluoroborate as the initiator. Incorporating ethylene oxide repeat units into the monomer is an effective method to induce Li-ion conductivity. The ethylene oxide units can effectively solvate a lithium salt, such as lithium perchlorate or lithium trifluoromethansulfanote, because of the electronegative oxygen atom. Additionally, the flexibility of the repeat units, with a glass transition temperature ($T_g$) generally below room temperature, facilitates the movement of the Li-ions between the electrodes. As described hereinabove, variation of the number of ethylene oxide units can allow for a level of control over the physical properties of the electropolymerized solid polymer electrolyte. As lithium-ions coordinate to multiple electronegative atoms, the moles of $Li^+$ per mole of monomer incorporated will be a function of the number of repeat units in the electrodeposited film. As an example, to ensure that Li-ions are being solvated in the film, the atomic ratio of oxygen to $Li^+$ should be approximately 6 to 1.

To prepare the samples, a substrate consisting of electrodeposited $Cu_2Sb$ is placed into a 5% by volume $HNO_3$ cleaning solution for approximately 5 s to remove surface oxides. It is subsequently submersed into an aqueous deposition solution consisting of 0.1 M sulfuric acid, 0.1 M $LiClO_4$ (which acts as the supporting electrolyte), and 0.005 M 4-methoxybenzenediazonium tetrafluoroborate. Dissolved $O_2$ (g) was removed by bubbling $N_2$ (g) through the aqueous solution. 0.4 M acrylonitrile was then added to the deposition and stirred thoroughly to ensure complete dissolution of the monomer. 0.3 M methyl acrylate was then added and also stirred thoroughly. Finally, the poly(ethylene) glycol methyl ether methacrylate was added to the deposition solution. The concentration of the poly(ethylene) glycol methyl ether methacrylate was varied and the concentration of the salt for each co-electropolymerization deposition solution is contained in TABLE 3.

TABLE 3

Co-electropolymerization of acrylonitrile (0.4M), methyl acrylate (0.3M), and poly(ethylene) glycol methyl ether methacrylate.

| Sample # | poly(ethylene) glycol methyl ether methacrylate (M) |
|---|---|
| PAN-MA-PEGMEMA-1 | 0 |
| PAN-MA-PEGMEMA-2 | 0.025 |
| PAN-MA-PEGMEMA-3 | 0.050 |

Figure 11:
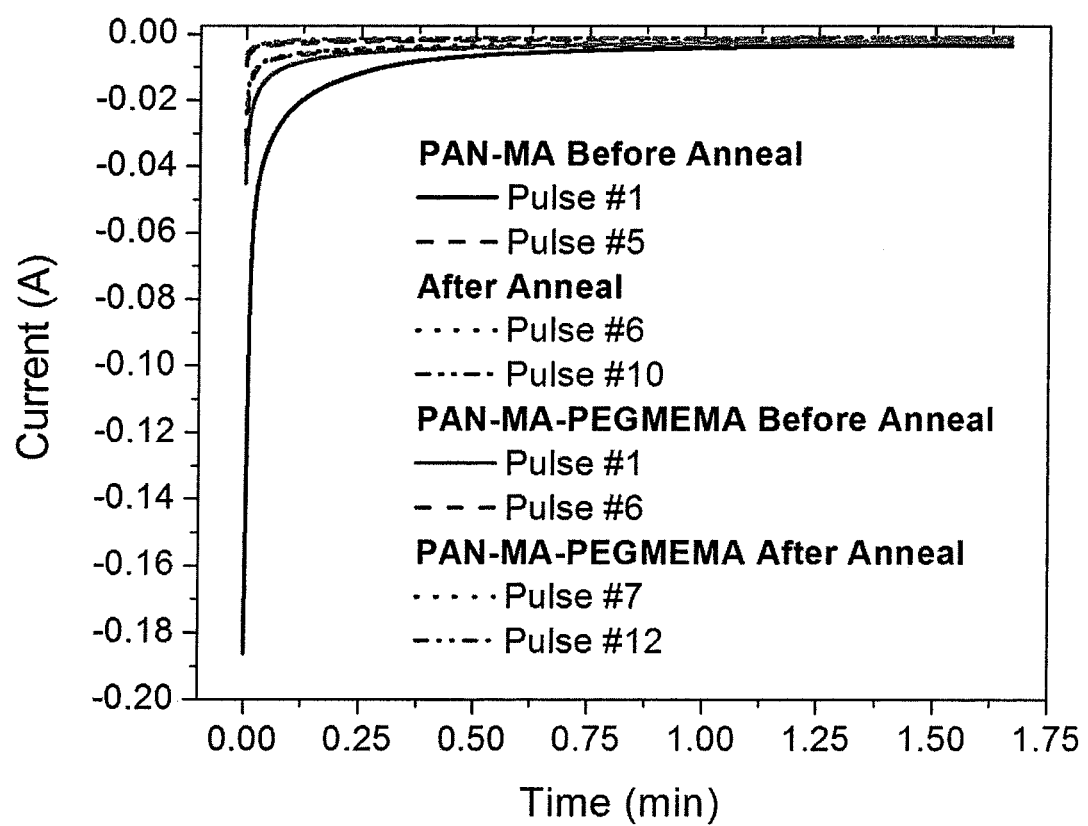
FIG. 11 shows selected chronoamperometry curves collected from a characteristic electropolymerization method consisting of ten, 100 s potentiostatic pulses at −0.65 V vs. Ag/AgCl applied to a $Cu_2Sb$ deposition substrate when submersed in an aqueous electropolymerization solution containing of 0.1 M sulfuric acid, 0.1 M $LiClO_4$, 0.005 M 4-methoxybenzenediazonium tetrafluoroborate, 0.4 M acrylonitrile, 0.3 M methyl acrylate, and poly(ethylene) glycol methyl ether methacrylate having various concentrations.

The co-electropolymerization is induced by applying a potential of −0.65 V vs. Ag/AgCl for six, 100 s potentiostatic pulses. Gas bubbles formed during the reduction of the 4-methoxybenzenediazonium tetrafluoroborate were removed between each pulse from the deposition substrate surface by removing and then subsequently re-submersing the substrate in the solution until the gas was completely removed. After completion of the electropolymerization pulses, the samples were placed into a vacuum at 100° C. for 1 h at approximately −25 mmHg. After the hour at 100° C., the samples were allowed to cool to room temperature before removing them from vacuum. This process was repeated to achieve the final copolymer film. The current profile resulting from these potentiostatic pulses with and without poly(ethylene) glycol methyl ether methacrylate in the deposition solution are contained in FIG. 11. To induce lithium-ion conductivity, the samples were submersed in an electrolyte solution consisting of 1 M $LiClO_4$ for times ranging from two hours to 12 h.

EXAMPLE 5

To demonstrate the implementation of the embodiments contained in this invention pertaining to the fabrication of a functional electrodeposited solid polymer electrolyte, copper antimonide ($Cu_2Sb$), which is a known negative electrode lithium intercalation material, was electrochemically deposited onto a copper foil substrate according to a known procedure. Samples described in EXAMPLES 2 and 3 were then prepared. The integrity of the films was then quantified. The positive electrode was applied directly to the electropolymerized polymer by coating with an aqueous slurry consisting of approximately 24.4 wt percent $LiCoO_2$, 6.2 wt percent carbon, 17.4 wt percent poly (ethylene glycol) with an average molecular weight of 3350 Daltons, 5.2 wt percent $LiClO_4$, and 45.8 wt percent water. While the slurry was still wet, an aluminum mesh was placed on top of the sample to act as the positive electrode current collector when dried. Once the water evaporated, the samples were dried further in a vacuum oven at approximately 100° C. for 1.5-2 h. The sample was then placed and sealed in a polycarbonate cell under argon. Argon was used because it is inert and will not interact with any of the components during the electrochemical lithiation and delithiation reactions.

Figure 12:
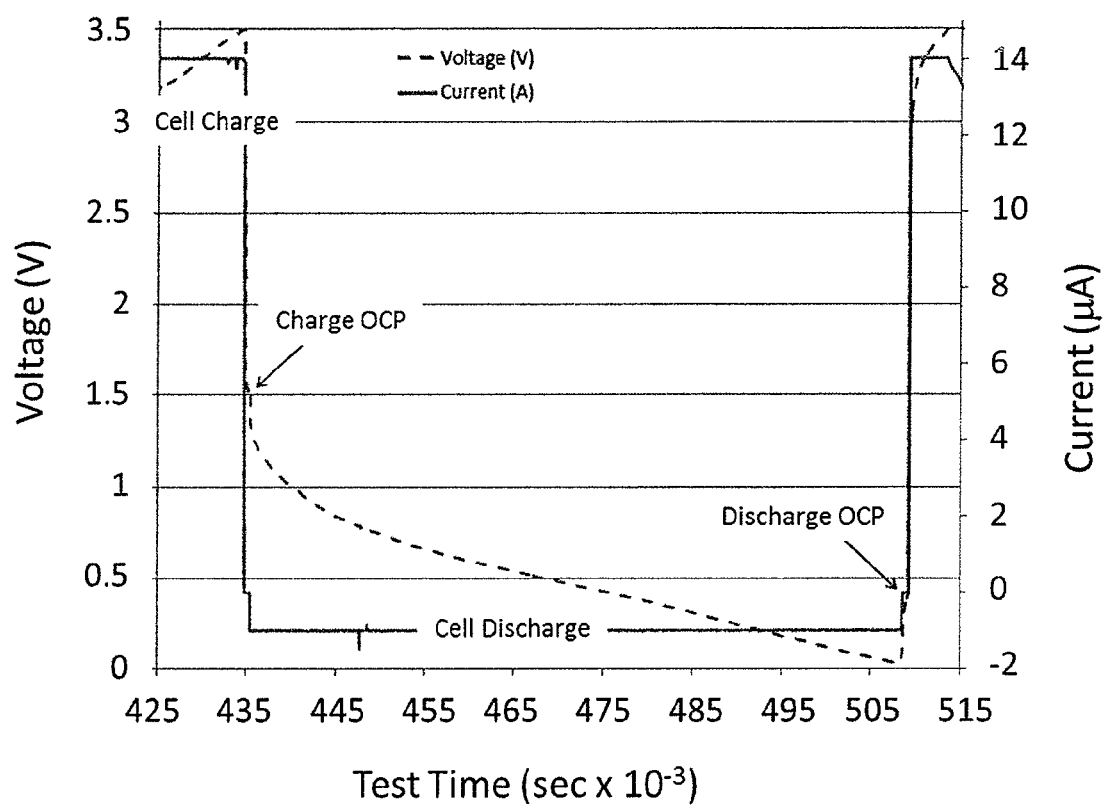
FIG. 12 shows a characteristic charge and discharge cycle for a functional solid-state lithium-ion cell consisting of $Cu_2Sb$ with an electropolymerized acrylonitrile/methyl acrylate solid polymer electrolyte coating with a $LiCoO_2$ based positive electrode directly applied to the surface of the polymer electrolyte coating.

To facilitate lithium-ion transport, the cells were placed in an oven at approximately 60° C. Once the temperature of the cell had reached steady state, a current of 14 µA was applied to the cell to charge the cell from the initial cell voltage of approximately 130 mV to 3.5 V. Once the voltage reached 3.5 V, the polarity of the current was flipped to −1 µA until the voltage decreased to a value of approximately 0 V. FIG. 12 illustrates data for a characteristic charge and discharge cycle for the above described cell and demonstrates that electrodeposited $Cu_2Sb$ with an electrodeposited layer of PAN-MA as the solid-state electrolyte using the aqueous slurry based $LiCoO_2$ cathode, described hereinabove. The large drop in potential when transitioning from the charge segment to recording the open circuit potential (OCP), which is a state of zero current, is attributed to a large impedance contact between the cathode slurry and the aluminum mesh current collector. To demonstrate the enhanced performance of an electropolymerized film containing sulfopropylacrylate salt, samples described in EXAMPLE 3 were prepared and placed in a carbonate cell as described hereinabove.

Figure 13:
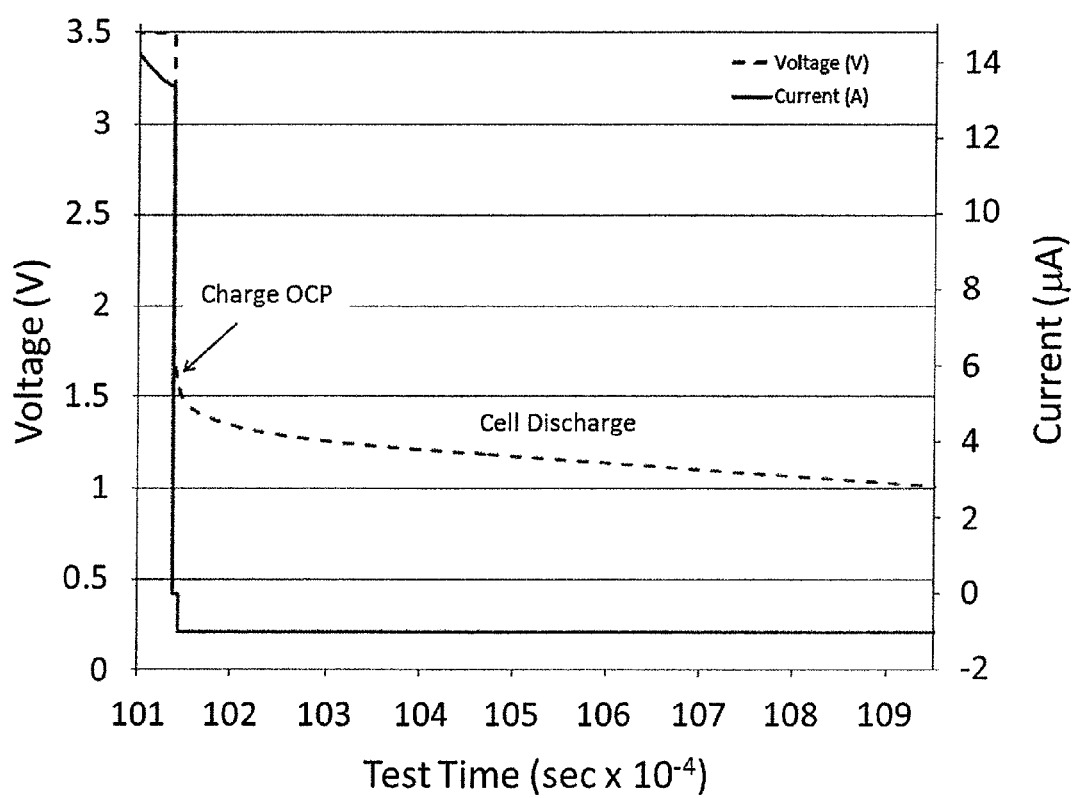
FIG. 13 shows a characteristic charge and discharge cycle for a functional solid-state lithium-ion cell comprising $Cu_2Sb$ with an electropolymerized acrylonitrile/methyl acrylate based solid polymer electrolyte coating for which sulfopropylacrylate salt was incorporated into the coating through the electropolymerization solution with a $LiCoO_2$ based positive electrode directly applied to the surface of the polymer electrolyte coating.
Figure 14:
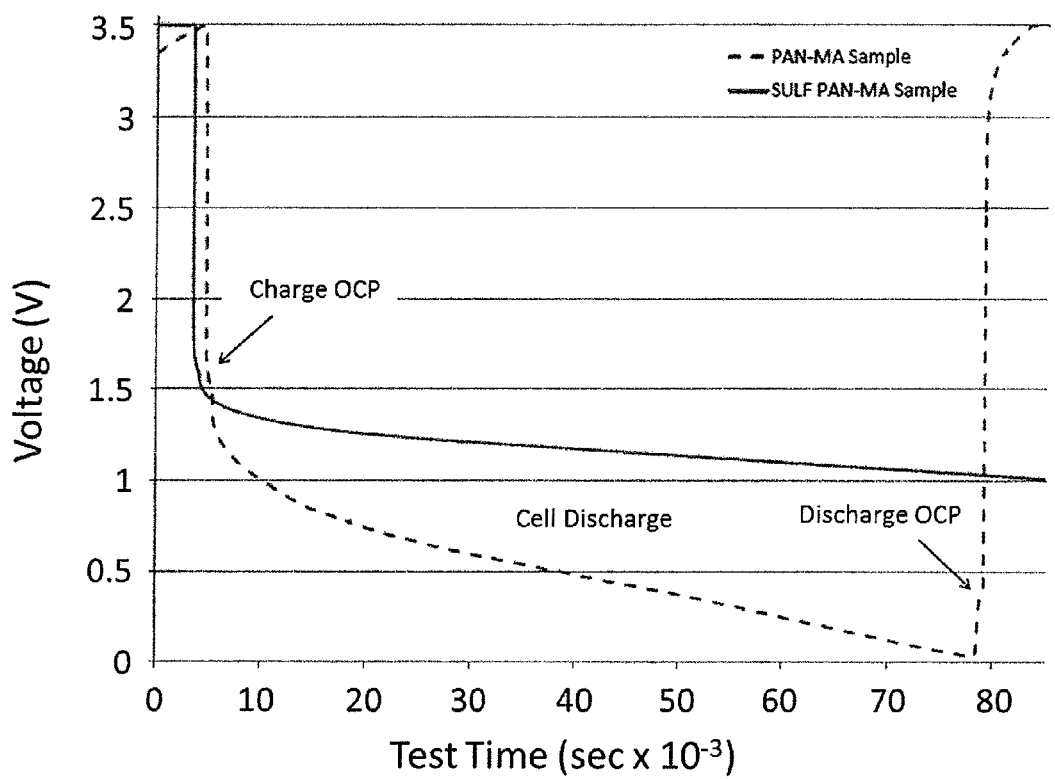
FIG. 14 shows an overlay of the voltage profiles associated with the functional solid-state lithium-ion cells for which one of the solid polymer electrolyte coatings contained sulfopropylacrylate salt and the other did not, the enhanced performance of the cell fabricated with sulfopropylacrylate salt as a constituent of the solid polymer electrolyte coating being demonstrated by a lower polarization voltage and increased capacity.

The performance of the cell can be further optimized by improving the lithium-ion transport through the solid-state electrolyte. This is accomplished by incorporating flexible lithium-ion host, in this case sulfonate groups, into the backbone of the acrylonitrile-methyl acrylate solid polymer electrolyte. When the sulfonate groups are incorporated into the polymer and the cell is assembled as described above, a measurable increase in the capacity of the overall cell is observed. FIG. 13 illustrates characteristic charge and discharge data from a sulfonate modified solid-state electrolyte cell. While a large drop is still observed during the charge OCP, it is not as extreme as that observed for the non-sulfonate solid-state electrolyte. Additionally, the discharge capacity for the sulfonate cells is much higher than the non-sulfonate cells. This is highlighted in FIG. 14 which shows data from both cells overlaid onto each other. When the non-sulfonate cell reaches approximately 0 V and thus begins the discharge OCP, the sulfonate sample is maintaining a potential one volt higher; thereby demonstrating the enhanced performance of the sulfonate containing solid polymer electrolyte.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for electrochemically depositing an ionically conducting, electrically insulating coating onto the surface of an electrode material, comprising:

submersing the electrode material into a solution comprising at least one initiator species dissolved in a solvent, wherein the at least one initiator species is capable of being reduced forming a radical species when an electron is injected from the electrode material into the initiator species, and wherein the at least one reduced initiator species is chemisorbed onto the electrode material surface; and at least one monomeric species having at least one vinyl group, or vinyl group derivative, thereon;

submersing a second electrode into the solution; and applying an electric potential between the electrode material and the second electrode effective for reducing the at least one initiator species;

whereby polymerization of the at least one monomeric species is induced by the reduction of the initiator species forming a coating which is bonded to the surface of the electrode material.

2. The method of claim 1, wherein the electric potential effective for reduction of the at least one initiator species on the surface of the electrode material is more positive than the electrochemical reduction potential of the solvent and more negative than the electrochemical oxidation potential of the electrode material.

3. The method of claim 1, further comprising the step of measuring the current flowing in the solution between the electrode material and the second electrode resulting from the applied electric potential, and extinguishing the applied electric potential when the current asymptotically reaches a non-zero steady state value.

4. The method of claim 1, wherein the at least one initiator species when reduced is covalently bonded to the surface of the electrode material.

5. The method of claim 4, wherein the coating is covalently bonded to the electrode material.

6. The method of claim 1, wherein the electrode material comprises $Cu_2Sb$.

7. The method of claim 6, wherein the solvent comprises water.

8. The method of claim 6, wherein the at least one initiator species comprises a diazonium species.

9. The method of claim 8, wherein the diazonium species is chosen from 4-methoxybenzenediazonium tetrafluoroborate, 4-nitrobenzenediazonium tetrafluoroborate, 4-poly(ethylene glycol)benzene diazonium tetrafluoroborate, 2-poly(ethylene glycol)benzene diazonium tetrafluoroborate, Lithium[4-(sulfonato)benzenediazonium]tetrafluoroborate, and Lithium[2-(sulfonato)benzenediazonium]tetrafluoroborate.

10. The method of claim 6, wherein the coating comprises a copolymer.

11. The method of claim 10, wherein the at least one monomeric species is chosen from acrylonitrile, methyl acrylate, acrylic acid, poly(ethylene glycol) methyl ether acrylate, and poly(ethylene glycol) methyl ether methacrylate.

12. The method of claim 1, wherein the at least one monomeric species comprises an ionic salt having $Li^+$ as the cation.

13. The method of claim 12, wherein the ionic salt comprises an anion portion chosen from sulfonate groups and carboxy groups.

14. The method of claim 12, wherein the ionic salt is chosen from lithium sulfopropylacrylate and lithium perfluoro-2-(2-sulfoethoxy) propyl vinyl ether.

15. The method of claim 12, wherein the anionic portion of the monomeric ionic salt is covalently bonded to the at least one vinyl group, or vinyl group derivative, by a tethering group having a chosen length.

16. The method of claim 15, wherein the tethering group is chosen from polyethylene oxide, polyethylene glycol, polypropylene oxide, polypropylene glycol, and alkanes, and fluorinated versions thereof having chosen lengths.

17. The method of claim 15, wherein the length of the tethering group is chosen to permit free motion of Li$^+$ ions through the coating, while preserving the solubility of the ionic monomer in the solvent.

18. The method of claim 12, wherein the coating is effective for transporting Li$^+$ ions therethrough.

19. The method of claim 1, further comprising the step of crosslinking the at least one monomeric species.

20. The method of claim 19, wherein said step of crosslinking the at least one monomeric species is achieved by adding at least one crosslinking monomer to the solution.

21. The method of claim 20, wherein said at least one crosslinking monomer is chosen from poly(ethylene glycol) diacrylate and bisphenol A ethoxylate dimethacrylate.

22. The method of claim 6, wherein the initiator comprises an organic halide.

23. The method of claim 22, wherein the organic halide comprises bromoisobutyronitrile.

24. The method of claim 1, further comprising the step of contacting the coating with a solution containing a lithium salt.

25. The method of claim 24, wherein the lithium salt is chosen from lithium perchlorate, lithium bis(trifluoromethane)sulfonamide, and lithium trifluoromethanesulfanate.

26. The method of claim 24 wherein the lithium salt is dissolved in water or acetonitrile.

27. The method of claim 1, further comprising the steps of: preparing a solution-based slurry comprising at least one cathode material; contacting the coating with the slurry; drying the coating material onto which the at least one cathode material has been deposited; and placing an electrode in electrical communication with the at least one cathode material.

28. The method of claim 27, wherein the at least one cathode material is chosen from LiFePO$_4$, LiCoO$_2$, LiMnO$_2$, LiNi$_{0.5}$Mn$_{1.5}$O$_4$, and LiNi$_{0.4}$CO$_{0.2}$Mn$_{1.4}$O$_4$.

29. The method of claim 27, wherein the slurry further comprises at least one polymer binder.

30. The method of claim 27, wherein the at least one polymer binder is chosen from polyethylene oxide, polyethylene glycol, polypropylene oxide, polypropylene glycol, and alcohol-based polymers, and copolymers thereof.

31. The method of claim 27, wherein the slurry further comprises at least one lithium-containing salt.

32. The method of claim 31, wherein the at least one lithium-containing salt is chosen from lithium perchlorate, lithium bis(trifluoromethane)sulfonamide, and lithium trifluoromethanesulfonate.

33. The method of claim 31 wherein the lithium salt is dissolved in water or acetonitrile.

34. The method of claim 27, wherein the slurry further comprises at least one lithium-ion conducting glass ceramic.

35. The method of claim 1, further comprising the steps of: placing the electrode material in electrical contact with a third electrode; submersing the third electrode in the solution before said step of submersing the electrode material into the solution, and before said step of applying an electric potential between the electrode material and the second electrode; and applying an electric potential between the electrode material and the second electrode before said step of submersing the electrode material into the solution.

36. The method of claim 1, further comprising the step of adding a supporting electrolyte salt to the solution for facilitating charge transport within the solution, wherein the electrolyte salt is not reactive within the electrochemical oxidation potential and electrochemical reduction potential of the solution solvent.

37. A method for producing a lithium-ion battery comprising:
submersing an electrode comprising electrodeposited Cu$_2$Sb active material into a solution comprising at least one initiator species dissolved in a solvent comprising water, wherein the at least one initiator species is capable of being reduced forming a radical species when an electron is injected from the Cu$_2$Sb active material into the initiator species, and wherein the at least one reduced initiator species is chemisorbed onto a surface of the Cu$_2$Sb active material; and at least one monomeric species having at least one vinyl group, or vinyl group derivative thereon;
submersing a second electrode into the solution;
applying an electric potential between the electrode material and the second electrode effective for reducing the at least one initiator species;
whereby polymerization of the at least one monomeric species is induced by the reduction of the initiator species forming a Li$^+$-conducting and electrically insulating coating which is bonded to the surface of the active material;
preparing an solution-based slurry comprising at least one cathode material;
contacting the coating with the slurry; drying the coating material onto which the at least one cathode material has been deposited; and
placing a current collector in electrical communication with the at least one cathode material.

38. The method of claim 37, wherein the at least one initiator species comprises a diazonium species.

39. The method of claim 38, wherein the diazonium species is chosen from 4-methoxybenzenediazonium tetrafluoroborate, 4-nitrobenzenediazonium tetrafluoroborate, 4-poly(ethylene glycol)benzene diazonium tetrafluoroborate, 2-poly(ethylene glycol)benzene diazonium tetrafluoroborate, Lithium[4-(sulfonato)benzenediazonium]tetrafluoroborate, and Lithium[2-(sulfonato)benzenediazonium]tetrafluoroborate, 4-poly(ethylene glycol)benzene diazonium tetrafluoroborate, 2-poly(ethylene glycol)benzene diazonium tetrafluoroborate, Lithium[4-(sulfonato)benzenediazonium] tetrafluoroborate, and Lithium[2-(sulfonato) benzenediazonium]tetrafluoroborate.

40. The method of claim 37, wherein the coating comprises a copolymer.

41. The method of claim 40, wherein the at least one monomeric species comprises acrylonitrile, methyl acrylate, acrylic acid, poly(ethylene glycol) methyl ether acrylate, and poly(ethylene glycol) methyl ether methacrylate.

42. The method of claim 37, wherein the at least one monomeric species comprises an ionic salt comprising an anion portion and having Li$^+$ as the cation.

43. The method of claim 42, wherein the anion portion chosen from sulfonate groups and carboxy groups.

44. The method of claim 42, wherein the ionic salt comprises lithium sulfopropylacrylate and lithium perfluoro-2-(2-sulfoethoxy) propyl vinyl ether.

45. The method of claim 42, wherein the anionic portion of the monomeric ionic salt is covalently bonded to the at least one vinyl group or vinyl group derivative by a tethering group having a chosen length.

46. The method of claim 45, wherein the tethering group is chosen from polyethylene oxide, polyethylene glycol, polypropylene oxide, polypropylene glycol, and alkanes, and fluorinated versions thereof, having chosen lengths.

47. The method of claim 45, wherein the length of the tethering group is chosen to permit free motion of Li$^+$ ions through the coating, while preserving the solubility of the ionic monomer in the solvent.

48. The method of claim 37, further comprising the step of crosslinking the at least one monomeric species.

49. The method of claim 48, wherein said step of crosslinking the at least one monomeric species is achieved by adding at least one crosslinking monomer to the solution.

50. The method of claim 49, wherein said at least one crosslinking monomer is chosen from poly(ethylene glycol) diacrylate and bisphenol A ethoxylate dimethacrylate.

51. The method of claim 37, wherein the initiator comprises an organic halide.

52. The method of claim 51, wherein the organic halide comprises bromoisobutyronitrile.

53. The method of claim 37, further comprising the step of contacting the coating with a solution containing a lithium salt.

54. The method of claim 53, wherein the lithium salt is chosen from lithium perchlorate, lithium bis(trifluoromethane)sulfonamide, and lithium trifluoromethanesulfanate.

55. The method of claim 53, wherein the lithium salt is dissolved in a solvent chosen from water and acetonitrile.

56. The method of claim 37, wherein the at least one cathode material is chosen from $LiFePO_4$, $LiCoO_2$, $LiMnO_2$, $LiNi_{0.5}Mn_{1.5}O_4$, and $LiNi_{0.4}Co_{0.2}Mn_{1.4}O_4$.

57. The method of claim 37, wherein the slurry further comprises at least one polymer binder.

58. The method of claim 57, wherein the at least one polymer binder is chosen from polyethylene oxide, polyethylene glycol, polypropylene oxide, polypropylene glycol, and alcohol-based polymers, and copolymers thereof.

59. The method of claim 37, wherein the slurry further comprises at least one lithium-containing salt.

60. The method of claim 59, wherein the at least one lithium-containing salt is chosen from lithium perchlorate, lithium bis(trifluoromethane)sulfonamide, and lithium trifluoromethanesulfonate.

61. The method of claim 37, wherein the slurry further comprises at least one lithium-ion conducting glass ceramic.

62. The method of claim 37, further comprising the steps of: placing the electrode material in electrical contact with a third electrode; submersing the third electrode in the solution before said step of submersing the electrode material into the solution, and before said step of applying an electric potential between the electrode material and the second electrode; and applying an electric potential between the electrode material and the second electrode before said step of submersing the electrode material into the solution.

* * * * *